United States Patent
Agutter et al.

(10) Patent No.: US 7,413,546 B2
(45) Date of Patent: Aug. 19, 2008

(54) METHOD AND APPARATUS FOR MONITORING DYNAMIC CARDIOVASCULAR FUNCTION USING N-DIMENSIONAL REPRESENTATIONS OF CRITICAL FUNCTIONS

(75) Inventors: James Agutter, Salt Lake City, UT (US); Noah Syroid, Salt Lake City, UT (US); Julio C. Bermudez, Salt Lake City, UT (US); Yinqi Zhang, Salt Lake City, UT (US); Michael E. Holmes, Muncie, IN (US); Frank Drews, Salt Lake City, UT (US); David Lee Strayer, Salt Lake City, UT (US); Robert William Albert, Salt Lake City, UT (US); Dwayne R. Westenskow, Salt Lake City, UT (US)

(73) Assignee: Univeristy of Utah Research Foundation, Salt Lake City, UT (US)

( * ) Notice: Subject to any disclaimer, the term of this patent is extended or adjusted under 35 U.S.C. 154(b) by 791 days.

(21) Appl. No.: 10/846,956

(22) Filed: May 14, 2004

(65) Prior Publication Data

US 2005/0010117 A1    Jan. 13, 2005

Related U.S. Application Data

(63) Continuation-in-part of application No. 09/689,225, filed on Oct. 10, 2000, now abandoned, which is a continuation-in-part of application No. 09/457,068, filed on Dec. 7, 1999, now abandoned.

(51) Int. Cl.
*A61B 5/02* (2006.01)
(52) U.S. Cl. .................................. 600/485
(58) Field of Classification Search ............... 600/485; 434/262–275
See application file for complete search history.

(56) References Cited

U.S. PATENT DOCUMENTS

| 3,908,640 A | 9/1975 | Page |
| 4,193,393 A | 3/1980 | Schlager |
| 4,464,122 A | 8/1984 | Fuller et al. |
| 4,519,395 A | 5/1985 | Hrushesky |
| 4,619,269 A | 10/1986 | Cutler et al. |

(Continued)

*Primary Examiner*—Robert L. Nasser, Jr.
*Assistant Examiner*—Karen E Toth
(74) *Attorney, Agent, or Firm*—Thorpe North & Western LLP

(57) ABSTRACT

A method, system, apparatus and device for the monitoring, diagnosis and evaluation of the state of a dynamic system is disclosed. This method and system provides the processing means for receiving sensed and/or simulated data, converting such data into a displayable object format and displaying such objects in a manner such that the interrelationships between the respective variables can be correlated and identified by a user. This invention provides for the rapid cognitive grasp of the overall state of a critical function with respect to a dynamic system. The system provides for displayed objects, which change in real-time to show the changes of the functions of the system. It is a highly flexible system which works with a wide variety of applications, including biological systems, environmental systems, engineering systems, economic systems, mechanical systems, chemical systems and the like. The device of this invention is adapted specifically to providing objects within a frame associated with other objects in a reference grid to provide a graphical representation of cardiovascular function.

23 Claims, 28 Drawing Sheets

U.S. PATENT DOCUMENTS

| | | |
|---|---|---|
| 4,832,038 A | 5/1989 | Arai et al. |
| 4,875,165 A | 10/1989 | Fencil et al. |
| 4,880,013 A | 11/1989 | Chio |
| 4,930,518 A | 6/1990 | Hrushesky |
| 4,989,611 A | 2/1991 | Zanetti et al. |
| 5,012,411 A | 4/1991 | Policastro et al. |
| 5,103,828 A | 4/1992 | Sramek |
| 5,121,469 A | 6/1992 | Richards et al. |
| 5,162,991 A | 11/1992 | Chio |
| 5,222,020 A | 6/1993 | Takeda |
| 5,224,481 A | 7/1993 | Ishahara et al. |
| 5,425,372 A | 6/1995 | Takeda |
| 5,568,811 A | 10/1996 | Olstad |
| 5,626,141 A | 5/1997 | Takeda |
| 5,634,461 A | 6/1997 | Faithfull et al. |
| 5,769,082 A | 6/1998 | Perel |
| 5,796,398 A | 8/1998 | Zimmer |
| 5,812,688 A | 9/1998 | Gibson |
| 5,823,958 A * | 10/1998 | Truppe .................. 600/426 |
| 5,836,884 A | 11/1998 | Chio |
| 5,884,016 A | 3/1999 | Allen et al. |
| 5,913,826 A | 6/1999 | Blank |
| 5,961,467 A | 10/1999 | Shimazu et al. |
| 6,042,548 A | 3/2000 | Giuffre |
| 6,090,047 A | 7/2000 | Kass et al. |
| 6,222,547 B1 | 4/2001 | Schwutke et al. |
| 6,484,048 B1 | 11/2002 | Hoshino et al. |
| 2003/0227472 A1* | 12/2003 | Westinskow et al. ........ 345/700 |
| 2005/0080323 A1* | 4/2005 | Kato ..................... 600/323 |

* cited by examiner

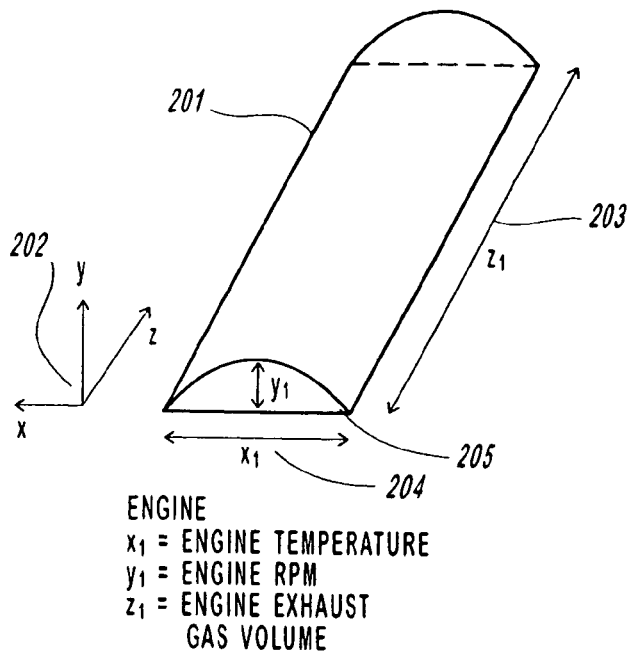

ENGINE
$x_1$ = ENGINE TEMPERATURE
$y_1$ = ENGINE RPM
$z_1$ = ENGINE EXHAUST GAS VOLUME

FIGURE 2a

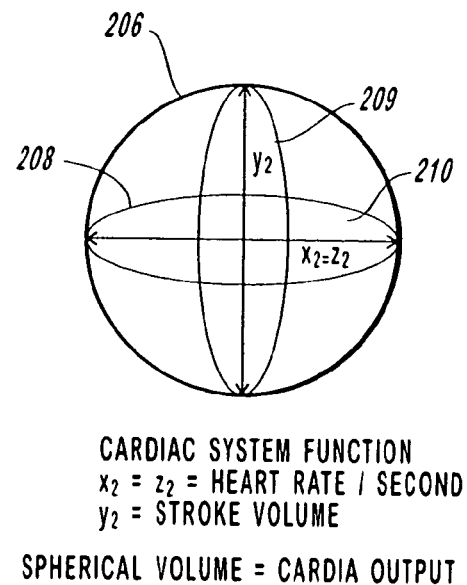

CARDIAC SYSTEM FUNCTION
$x_2 = z_2$ = HEART RATE / SECOND
$y_2$ = STROKE VOLUME

SPHERICAL VOLUME = CARDIA OUTPUT

FIGURE 2b

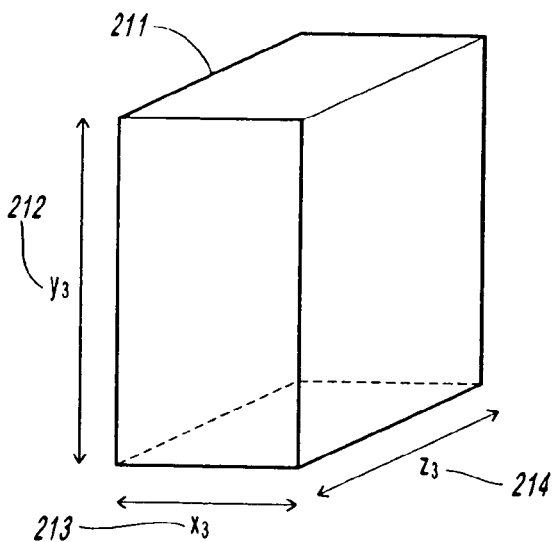

SALES DEPARTMENT OPERATION
$x_3$ = AVERAGE TIME / CONTRACT
$y_3$ = # OF CONTRACTS
$z_3$ = AVG. REVENUE/CONTRACT

FIGURE 2c

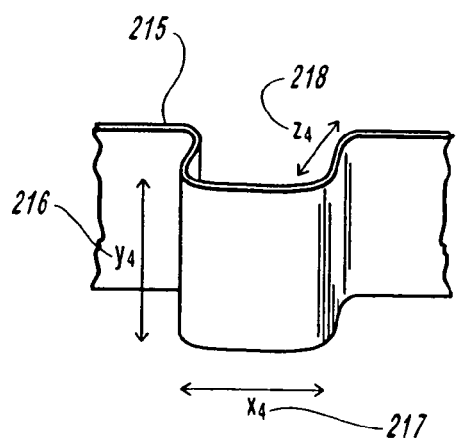

RESPIRATORY FUNCTION
$x_4$ = AVERAGE TIME / CONTRACT
$y_4$ = FCN OF xy AND RESP. VOLUME
$z_4$ = +/- INHALATION / EXHALATION
SLAB VOLUME = RESPIRATORY VOLUME

FIGURE 2d

| INTERFACE MODE I<br>(e.g. MEDICINE) | INTERFACE MODE II<br>(e.g. CORPORATE DASHBOARD) |
|---|---|
| GIVEN:<br>  - CRITICAL FUNCTIONS<br>(UNCHANGEABLE)<br>  - PHYSIOLOGIC DATA COLLECTED<br>  - SYMBOLIC SYSTEM STANDARD<br>  - REFERENTIAL FRAMEWORK<br>    IDEAL VALUES/ALARMS<br>(CHANGEABLE)<br>  - PARTICULAR VALUES<br>  - OBJECT ATTRIBUTES<br>1301 | GIVEN:<br>  - DEFAULT/GENERIC L-SPACE/H-SPACE<br>USER DETERMINES:<br>  - CRITICAL FUNCTIONS<br>  - VITAL SIGNS TO BE COLLECTED<br>  - SYMBOLIC SYSTEM TO BE USED<br>  - IDEAL VALUES/ALARMS<br>  - OBJECTS/ATTRIBUTES SPACE<br>1302 |

COMMON INTERFACE FEATURES
- L-SPACE
- H-SPACE
- ZOOM/SPEED
- VIEWPOINTS

FIGURE 13

METHOD AND APPARATUS FOR MONITORING DYNAMIC CARDIOVASCULAR FUNCTION USING N-DIMENSIONAL REPRESENTATIONS OF CRITICAL FUNCTIONS

This Continuation-In-Part application claims priority to U.S. application Ser. No. 09/689,225 filed Oct. 10, 2000 now abandoned which is a Continuation-In-Part patent application of U.S. patent application Ser. No. 09/457,068 filed Dec. 7, 1999 now abandoned.

BACKGROUND OF THE INVENTION

1. Field of the Invention

This invention relates to the visualization, perception, representation and computation of data relating to the attributes or conditions constituting the health state of a dynamic system. More specifically, this invention relates to the display and computation of cardiovascular data, in which variables constituting attributes and conditions of a dynamic physiological system can be interrelated and visually correlated in time as three-dimensional objects.

2. Description of the Related Art

A variety of methods and systems for the visualization of data have been proposed. Traditionally, these methods and systems fail to present in a real-time multi-dimensional format that is directed to facilitating a user's analysis of multiple variables and the relationships between such multiple variables. Moreover, such prior methods and systems tend not to be specifically directed to display of a patient's cardiovascular system by showing such cardiovascular variables as blood pressure, blood flow, vascular tone and the like. Prior methods typically do not process and display data in real-time, rather they use databases or spatial organizations of historical data. Generally, they also simply plot existing information in two or three dimensions, but without using three-dimensional geometric objects to show the interrelations between data. Often previous systems and methods are limited to pie charts, lines or bars to represent the data. Also, many previous systems are limited to particular applications or types of data. The flexibility and adaptability of the user interface and control is typically very limited, and may not provide flexible coordinate systems and historical-trend monitors. Other systems, which have a flexible user interface, generally require substantial user expertise in order to collect and evaluate the data, including the pre-identification of data ranges and resolution. Another common limitation of previous systems and methods is that they provide only a single or predetermined viewpoint from which to observe the data. Typically, prior systems and methods do not provide data normalcy frameworks to aid in the interpretation of the data. Furthermore, most prior methods use "icons," shapes, lines, bars, or graphs. For general background material, the reader is directed to U.S. Pat. Nos. 3,908,640, 4,193,393, 4,464,122, 4,519,395, 4,619,269, 4,752,893, 4,772,882, 4,813,013, 4,814,755, 4,823,283, 4,832,038, 4,875,165, 4,880,013, 4,915,757, 4,930,518, 4,989,611, 5,012,411, 5,021,976, 5,103,828, 5,121,469, 5,162,991, 5,222,020, 5,224,481, 5,262,944, 5,317,321, 5,425,372, 5,491,779, 5,568,811, 5,588,104, 5,592,195, 5,596,694, 5,626,141, 5,634,461, 5,751,931, 5,768,552, 5,774,878, 5,796,398, 5,812,134, 5,830,150, 5,836,884, 5,913,826, 5,923,330, 5,961,467, 6,042,548, and 6,090,047each of which is hereby incorporated by reference in its entirety for the material disclosed therein.

As this disclosure employs a number of terms, which may be new to the reader, the reader is directed to the applicants' definitions section, which is provided at the beginning of the detailed description section.

SUMMARY OF THE INVENTION

It is desirable to provide a method, system, and apparatus, which facilitates the rapid and accurate analysis of complex and quickly changing data. Moreover, it is desirable that such a system and method include a graphic element that depicts the status of a patient's cardiovascular system by graphically showing blood pressure, blood flow, vascular tone and other cardiovascular variables. It is important that such a graphic element provide an anesthesiologist with the means to quickly assess the patient's status. It is also desirable that the element by comprised of subcomponents, which are linked together to show thereby the relationships of the various cardiovascular variables. Also, it is desirable that system and method be capable of analyzing time based, real-time, and historical data and that it be able to graphically show the relationships between various data.

Research studies have indicated that the human mind is better able to analyze and use complex data when it is presented in a graphic, real world type representation, rather than when it is presented in textual or numeric formats. Research in thinking, imagination and learning has shown that visualization plays an intuitive and essential role in assisting a user associate, correlate, manipulate and use information. The more complex the relationship between information, the more critically important is the communication, including audio and visualization of the data. Modern human factors theory suggests that effective data representation requires the presentation of information in a manner that is consistent with the perceptual, cognitive, and response-based mental representations of the user. For example, the application of perceptual grouping (using color, similarity, connectedness, motion, sound etc.) can facilitate the presentation of information that should be grouped together. Conversely, a failure to use perceptual principles in the appropriate ways can lead to erroneous analysis of information.

The manner in which information is presented also affects the speed and accuracy of higher-level cognitive operations. For example, research on the "symbolic distance effect" suggests that there is a relationship between the nature of the cognitive decisions (for example, is the data increasing or decreasing in magnitude?) and the way the information is presented (for example, do the critical indices become larger or smaller, or does the sound volume or pitch rise or fall?). Additionally, "population stereotypes" suggest that there are ways to present information that are compatible with well-learned interactions with other systems (for example, an upwards movement indicates an increasing value, while a downwards movement indicates a decreasing value).

Where there is compatibility between the information presented to the user and the cognitive representations presented to the user, performance is often more rapid, accurate, and consistent. Therefore, it is desirable that information be presented to the user in a manner that improves the user's ability to process the information and minimizes any mental transformations that must be applied to the data.

Therefore, it is the general object of this invention to provide a method and systems for presenting a three-dimensional visual and/or possibly an audio display technique that assists a doctor in the monitoring of a patient's cardiovascular function.

It is a further object of this invention to provide a method and system that assists in the monitoring of a patient's cardiovascular system through the use of a three-dimensional graphic element.

It is another object of this invention to provide a method and system that assists in the management of anesthesia care of patients, by presenting a display, which quickly shows the relationships of various cardiovascular variables.

It is a still further object of this invention to provide a method and system that assists in the determination of the "health" of a dynamic cardiovascular system, by providing visual information related to the nature or quality of the soundness, wholeness, or well-being of the system as related to historical or normative values.

Another object of this invention is to provide a method and system that assists in the determination of the functioning of a cardiovascular system by measuring the interaction among a set of "vital-signs" normally associated with the health of the cardiovascular system.

A still further object of this invention is to provide a method and system, which provides the gathering and use of sensor measured data, as well as the formatting and normalization of the data in a format suitable to the processing methodology.

A further object of this invention is to provide a method and system, which organizes a cardiovascular system's data into relevant data sets or critical functions as appropriate.

Another object of this invention is to provide a method and system, which provides a three-dimensional health-space for mapping the cardiovascular system data.

It is another object of this invention to provide a method and system, which provides three-dimensional objects that are symbols of the critical functioning of the cardiovascular system being monitored.

It is an object of this invention to provide a method and system that shows the relationships between several critical functions that a user wishes to monitor.

It is a further object of this invention to provide a method and system that permits an integrated and overall holistic understanding of the cardiovascular process being monitored.

A further object of this invention is to provide a method and system where three-dimensional objects are built from three-dimensional object primitives, including: cubes, spheres, pyramids, n-polygon prisms, cylinders, slabs.

A still further object of this invention is to provide a method and system, wherein three-dimensional objects are placed within health-space based on the coordinates of their geometric centers, edges, vertices, or other definite geometric variables.

It is a further object of this invention to provide a method and system, which has three-dimensional objects that have three spatial dimensions, as well as geometric, aesthetic and aural attributes, to permit the mapping of multiple data functions.

It is another object of this invention to provide a method and system, which shows increases and decreases in data values using changes in location, size, form, texture, opacity, color, sound and the relationships thereof in their context.

It is a still further object of this invention to provide a method and system, wherein the particular three-dimensional configuration of three-dimensional objects can be associated with a particular time and health state.

A still further object of this invention is to provide a method and system that permits the simultaneous display of the history of data objects.

Another object of this invention is to provide a method and system that provides for the selection of various user selectable viewports.

It is a further object of this invention to provide a method and system that provides both a global and a local three-dimensional coordinate space.

It is another object of this invention to provide a method and system that permits the use of time as one of the coordinates.

It is a still further object of this invention to provide a method and system that provides a reference framework of normative values for direct comparison with the measured data.

It is a further object of this invention to provide a method and system where normative values are based on the average historical behavior of a wide population of healthy systems similar to the system whose health is being monitored.

A further object of this invention is to provide a method and system that provides viewpoints that can be selected to be perspective views, immersive Virtual Reality views, or any orthographic views.

Another object of this invention is to provide a method and system that permits the display of a layout of multiple time-space viewpoints.

A still further object of this invention is to provide a method and system that provides for zooming in and out of a time and/or space coordinate.

It is another object of this invention to provide a method and system that permits temporal and three-dimensional modeling of data "health" states based on either pre-recorded data or real-time data, that is as the data is obtained.

Another object of this invention is to provide a method and system that presents the data in familiar shapes, colors, and locations to enhance the usability of the data.

A still further object of the invention is to provide a method and system that uses animation, and sound to enhance the usefulness of the data to the user.

It is an object of this invention to provide a method and system for the measurement, computation, display and user interaction, of complex data sets that can be communicated and processed at various locations physically remote from each other, over a communication network, as necessary for the efficient utilization of the data and which can be dynamically changed or relocated as necessary.

It is a still further object of this invention to provide a method and system for the display of data that provides both a standard and a customized interface mode, thereby providing user and application flexibility.

These and other objects of this invention are achieved by the method and system herein described and are readily apparent to those of ordinary skill in the art upon careful review of the following drawings, detailed description and claims.

BRIEF DESCRIPTION OF THE DRAWINGS

In order to show the manner that the above recited and other advantages and objects of the invention are obtained, a more particular description of the preferred embodiment of the invention, which is illustrated in the appended drawings, is described as follows. The reader should understand that the drawings depict only a preferred embodiment of the invention, and are not to be considered as limiting in scope. A brief description of the drawings is as follows:

FIGS. 2a, 2b, 2c, and 2d are representative 3-D objects representing critical functions.

FIG. 13 shows the interface modes of the preferred embodiment of this invention.

Figure 1A:
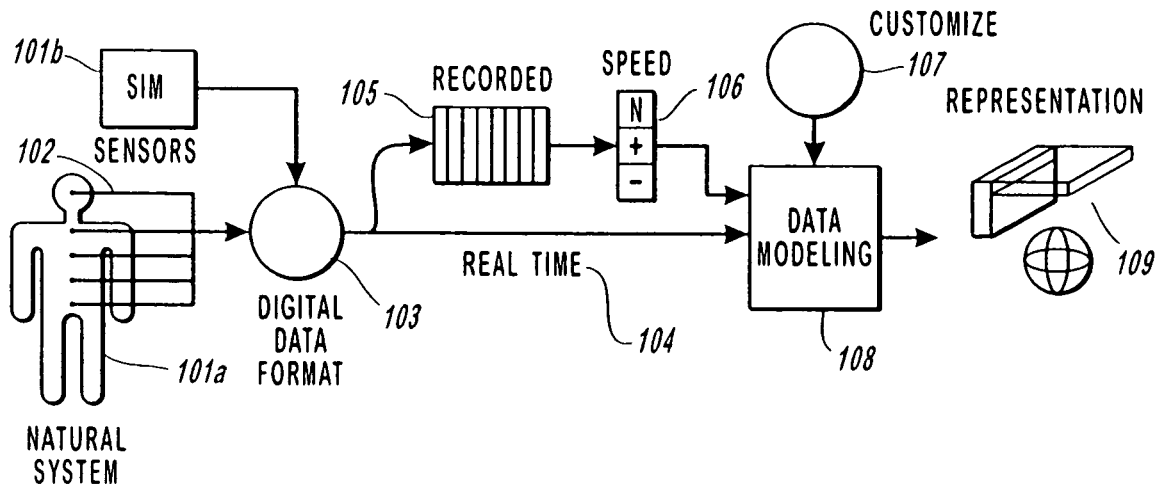
FIG. 1a is a top-level representative diagram showing the data processing paths of the preferred embodiment of this invention.

Reference will now be made in detail to the present preferred embodiment of the invention, examples of which are illustrated in the accompanying drawings.

DETAILED DESCRIPTION OF THE INVENTION

This invention is a method, system and apparatus for the visual display of complex sets of dynamic data. In particular, this invention provides the means for efficiently analyzing, comparing and contrasting data, originating from either natural or artificial systems. In its most common use the preferred embodiment of this invention is used to produce an improved cardiovascular display of a human or animal patient. This invention provides n-dimensional visual representations of data through innovative use of orthogonal views, form, space, frameworks, color, shading, texture, transparency, sound and visual positioning of the data. The preferred system of this invention includes one or a plurality of networked computer processing and display systems, which provide real-time as well as historical data, and which processes and formats the data into an audio-visual format with a visual combination of objects and models with which the user can interact to enhance the usefulness of the processed data. While this invention is applicable to a wide variety of data analysis applications, one important application is the analysis of health data. For this reason, the example of a medical application for this invention is used throughout this description. The use of this example is not intended to limit the scope of this invention to medical data analysis applications only, rather it is provided to give a context to the wide range of potential application for this invention.

This invention requires its own lexicon. For the purposes of this patent description and claims, the inventors intend that the following terms be understood to have the following definitions.

An "artificial system" is an entity, process, combination of human designed parts, and/or environment that is created, designed or constructed by human intention. Examples of artificial systems include manmade real or virtual processes, computer systems, electrical power systems, utility and construction systems, chemical processes and designed combinations, economic processes (including, financial transactions), agricultural processes, machines, and human designed organic entities.

A "natural system" is a functioning entity whose origin, processes and structures were not manmade or artificially created. Examples of natural systems are living organisms, ecological systems and various Earth environments.

The "health" of a system is the state of being of the system as defined by its freedom from disease, ailment, failure or inefficiency. A diseased or ill state is a detrimental departure from normal functional conditions, as defined by the nature or specifications of the particular system (using historical and normative statistical values). The health of a functioning system refers to the soundness, wholeness, efficiency or well being of the entity. Moreover, the health of a system is determined by its functioning.

"Functions" are behaviors or operations that an entity performs. Functional fitness is measures by the interaction among a set of "vital-signs" normally taken or measured using methods well known in the art, from a system to establish the system's health state, typically at regular or defined time intervals.

"Health-space" or "H-space" is the data representation environment that is used to map the data in three or more dimensions.

"H-state" is a particular 3-D configuration or composition that the various 3-D objects take in H-space at a particular time. In other words, H-state is a 3-D snapshot of the system's health at one point of time.

"Life-space" or "L-space" provides the present and past health states of a system in a historical and comparative view of the evolution of the system in time. This 3-D representation environment constitutes the historical or Life-space of a dynamic system. L-space allows for both continuous and categorical displays of temporal dependent complex data. In other words, L-space represents the health history or trajectory of the system in time.

"Real-Time Representation" is the display of a representation of the data within a fraction of a second from the time when the event of the measured data occurred in the dynamic system.

"Real-Time User Interface" is the seemingly instantaneous response in the representation due to user interactivity (such as rotation and zooming).

A "variable" is a time dependent information unit (one unit per time increment) related to sensing a given and constant feature of the dynamic system.

"Vital signs" are key indicators that measure the system's critical functions or physiology.

In the preferred embodiments of this invention, data is gathered using methods or processes well known in the art or as appropriate and necessary. For example, in general, physiologic data, such as heart rate, respiration rate and volume, blood pressure, and the like, is collected using the various sensors that measure the functions of the natural system. Sensor-measured data is electronically transferred and translated into a digital data format to permit use by the invention. This invention uses the received measured data to deliver real-time and/or historical representations of the data and/or recorded data for later replay. Moreover, this invention permits the monitoring of the health of a dynamic system in a distributed environment. By distributed environment, it is meant that a user or users interacting with the monitoring system may be in separate locations from the location of the dynamic system being monitored. In its most basic elements, the monitoring system of this invention has three major logical components: (1) the sensors that measure the data of the system; (2) the networked computational information systems that computes the representation and that exchanges data with the sensors and the user interface; and (3) the interactive user interface that displays the desired representation and that interactively accepts the users' inputs. The components and devices that perform the three major functions of this invention may be multiple, may be in the same or different physical locations, and/or may be assigned to a specific process or shared by multiple processes.

FIG. 1a is a top-level representative diagram showing the data processing paths of the preferred embodiment of this invention operating on a natural system. The natural system 101a is shown as a dynamic entity whose origin, processes and structures (although not necessarily its maintenance) were not manmade or artificially created. Examples of natural systems are living organisms, ecological systems, and various Earth environments. In one preferred embodiment of the invention, a human being is the natural system whose physiology is being monitored. Attached to the natural system 101a are a number of sensors 102. These sensors 102 collect the physiologic data, thereby measuring the selected critical functions of the natural system. Typically, the data gathering of the sensors 102 is accomplished with methods or techniques well known in the art. The sensors 102 are typically and preferably electrically connected to a digital data formatter 103. However, in other embodiments of this invention, the sensors may be connected using alternative means including but not limited to optical, RF and the like. In many instances, this digital data formatter 103 is a high-speed analog to digital converter. Also, connected to the digital data formatter 103 is the simulator 101b. The simulator 101b is an apparatus or process designed to simulate the physiologic process underlying the life of the natural system 101a. A simulator 101b is provided to generate vital sign data in place of a natural system 101a, for such purposes as education, research, system test, and calibration. The output of the digital data formatter 103 is Real-Time data 104. Real-Time data 104 may vary based on the natural system 101a being monitored or the simulator 101b being used and can be selected to follow any desired time frame, for example time frames ranging from one-second periodic intervals, for the refreshment rates of patients in surgery, to monthly statistics reporting in an ecological system. The Real-Time data 104 is provided to a data recorder 105, which provides the means for recording data for later review and analysis, and to a data modeling processor and process 108. In the preferred embodiments of this invention the data recorder 105 uses processor controlled digital memory, and the data modeling processor and process 108 is one or more digital computer devices, each having a processor, memory, display, input and output devices and a network connection. The data recorder 105 provides the recorded data to a speed controller 106, which permits the user to speed-up or slow-down the replay of recorded information. Scalar manipulations of the time (speed) in the context of the 3-D modeling of the dynamic recorded digital data allows for new and improved methods or reviewing the health of the systems 101a,b. A customize/standardize function 107 is provided to permit the data modeling to be constructed and viewed in a wide variety of ways according to the user's needs or intentions. Customization 107 includes the ability to modify spatial scale, such modifying includes but is not limited to zooming, translating, and rotating, attributes and viewports in addition to speed. In one preferred embodiment of the invention, the range of customization 107 permitted for monitoring natural systems 101a physiologic states is reduced and is heavily standardized in order to ensure that data is presented in a common format that leads to common interpretations among a diverse set of users. The data modeling processor and process 108 uses the prescribed design parameters, the standardized/customize function and the received data to build a three-dimensional (3-D) model in real-time and to deliver it to an attached display. The attached display of the data modeling processor and process 108 presents a representation 109 of 3-D objects in 3-D space in time to provide the visual representation of the health of the natural system 101a in time, or as in the described instances of the simulated 101b system.

Figure 1B:
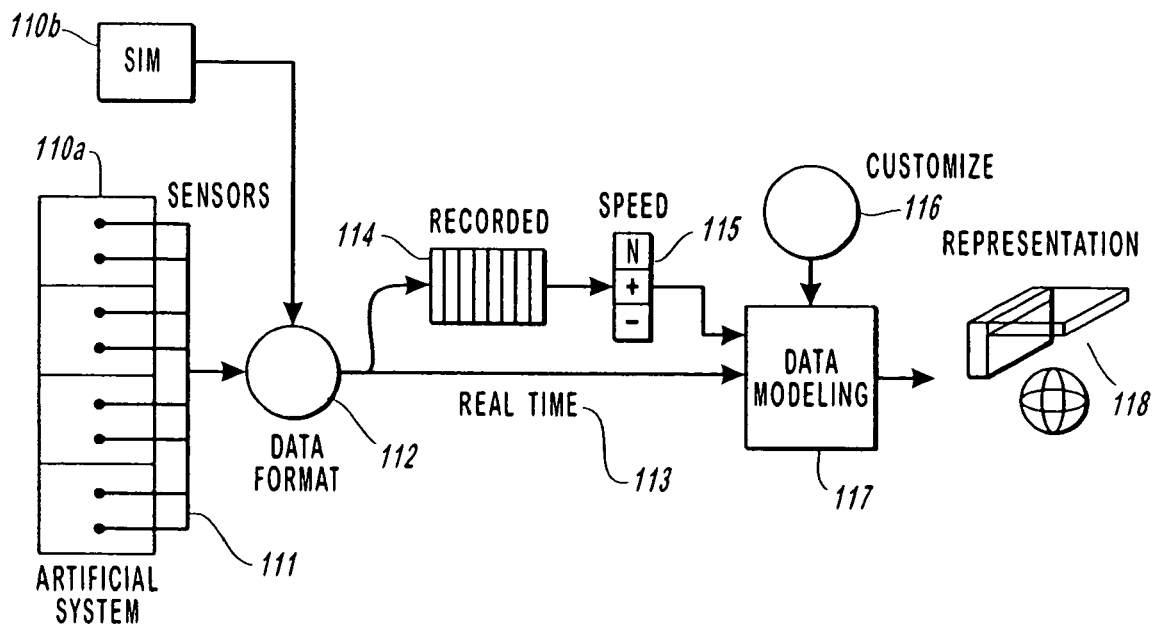
FIG. 1b is a top-level block diagram of the data processing flow of the preferred embodiment of this invention.

FIG. 1b is a top-level block diagram of the data processing flow of the preferred embodiment of this invention operating on an artificial system. An artificial system is a dynamic entity whose origin, processes and structure have been designed and constructed by human intention. Examples of artificial systems are manmade real or virtual, mechanical, electrical, chemical and/or organic entities. The artificial system 110a is shown attached to a number of sensors 111. These sensors 111 collect the various desired data, thereby measuring the selected critical functions of the artificial system. Typically, the data gathering of the sensors 111 is accomplished with methods or techniques well known in the art. The sensors 111 are connected to a data formatter 112, although alternative connection means including optical, RF and the like may be substituted without departing from the concept of this invention. In many instances, this digital data formatter 112 is a high-speed analog to digital converter. Although, in certain applications of the invention, namely stock market transactions, the data is communicated initially by people making trades. Also connected to the digital data formatter 112 is the simulator 110b. The simulator 110b is an apparatus or process designed to simulate the process underlying the state of the artificial system 110a. The simulator 110b is provided to generate vital data in place of the artificial system 110a, for such purposes as education, research, system test, and calibration. The output of the digital data formatter 112 is Real-Time data 113. Real-Time data 113 may vary based on the artificial system 110a being monitored or the simulator 110b being used and can be selected to follow any desired time frame, for example time frames ranging from microsecond periodic intervals, for the analysis of electronic systems, to daily statistics reported in an financial trading system. The Real-Time data 113 is provided to a data recorder 114, which provides the means for recording data for later review and analysis, and to a data modeling processor and process 117. In the preferred embodiments of this invention the data recorder 114 uses processor controlled digital memory, and the data modeling processor and process 117 is one or more digital computer devices, each having a processor, memory, display, input and output devices and a network connection. The data recorder 114 provides the recorded data to a speed controller 115, which permits the user to speed-up or slow-down the replay of recorded information. Scalar manipulations of the time (speed) in the context of the 3-D modeling of the dynamic recorded digital data allows for new and improved methods or reviewing the health of the system 110a,b. A customize/standardize function 116 is provided to permit the data modeling to be constructed and viewed in a wide variety of ways according to the user's needs or intentions. Customization 116 includes the ability to modify spatial scale (such modification including, but not limited to translating, rotating, and zooming), attributes, other structural and symbolic parameters, and viewports in addition to speed. The range of customization form monitoring artificial systems' 110a,b states is wide and not as standardized as that used in the preferred embodiment of the natural system 101a,b monitoring. In this Free Customization, the symbolic system and display method is fully adaptable to the user's needs and interests. Although this invention has a default visualization space, its rules, parameters, structure, time intervals, and overall design are completely customizable. This interface mode customize/standardize function 116 also allows the user to select what information to view and how to display the data. This interface mode customization 116 may, in some preferred embodiments, produce personalized displays that although they may be incomprehensible to other users, facilitate highly individual or competitive pursuits not limited to standardized interpretations, and therefore permit a user to look at data in a new manner. Such applications as analysis of stock market data or corporation health monitoring may be well suited to the flexibility of this interface mode. The data modeling processor and process 117 uses the prescribed design parameters, the customize/standardized function 116 and the received real-time data 113 to build a three-dimensional (3-D) model in time and to deliver it to a display. The display of the data modeling processor and process 117 presents a representation 118 of 3-D objects in 3-D space in time to provide the visual representation of the health of the artificial system 110a in time, or as in the described instances of the simulated 110b system.

Figure 1C:
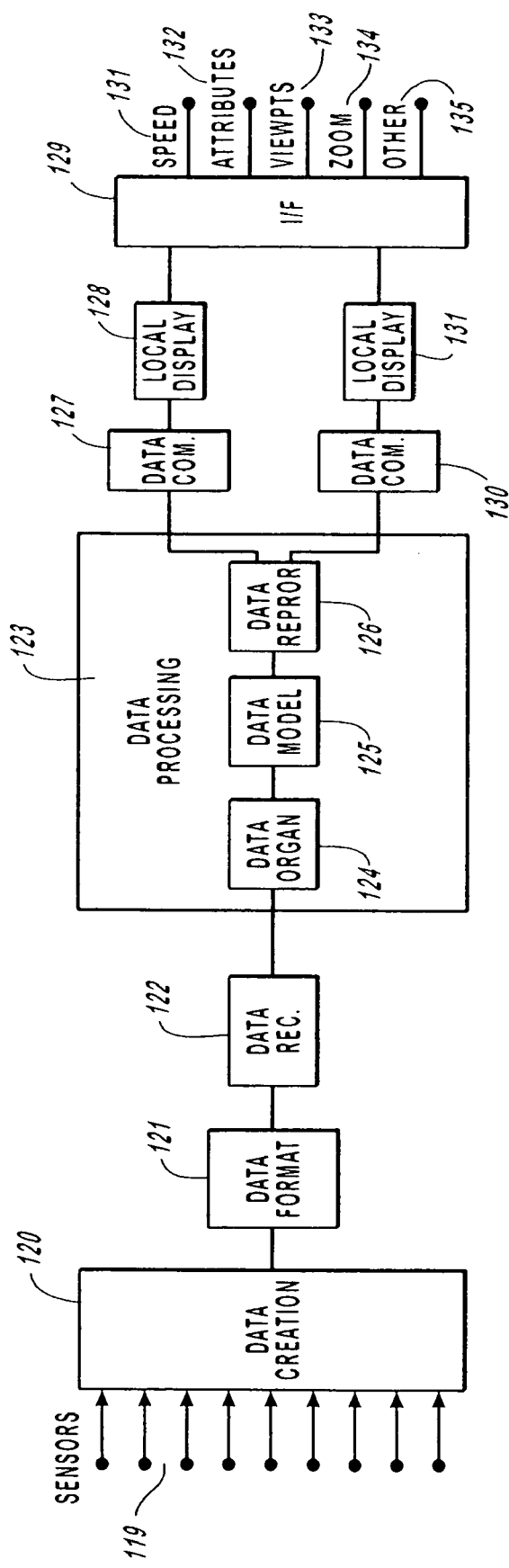
FIG. 1c is a top-level block diagram of one preferred processing path of this invention.

FIG. 1c is a top-level block diagram of one preferred processing path of this invention. Sensors 119 collect the desired signals and transfer them as electrical impulses to the appropriate data creation apparatus 120. The data creation apparatus 120 converts the received electrical impulses into digital data. A data formatter 121 receives the digital data from the data creation apparatus 120 to provide appropriate formatted data for the data recorder 122. The data recorder 122 provides digital storage of data for processing and display. A data processor 123 receives the output from the data recorder 122. The data processor 123 includes a data organizer 124 for formatting the received data for further processing. The data modeler 125 receives the data from the data organizer and prepares the models for representing to the user. The computed models are received by the data representer 126, which formats the models for presentation on a computer display device. Receiving the formatted data from the data processor 123 are a number of data communication devices 127, 130. These devices 127, 130 include a central processing unit, which controls the image provided to one or more local displays 128, 131. The local displays may be interfaced with a custom interface module 129 which provides user control of such attributes as speed 131, object attributes 132, viewports 133, zoom 134 and other like user controls 135.

Figure 1D:
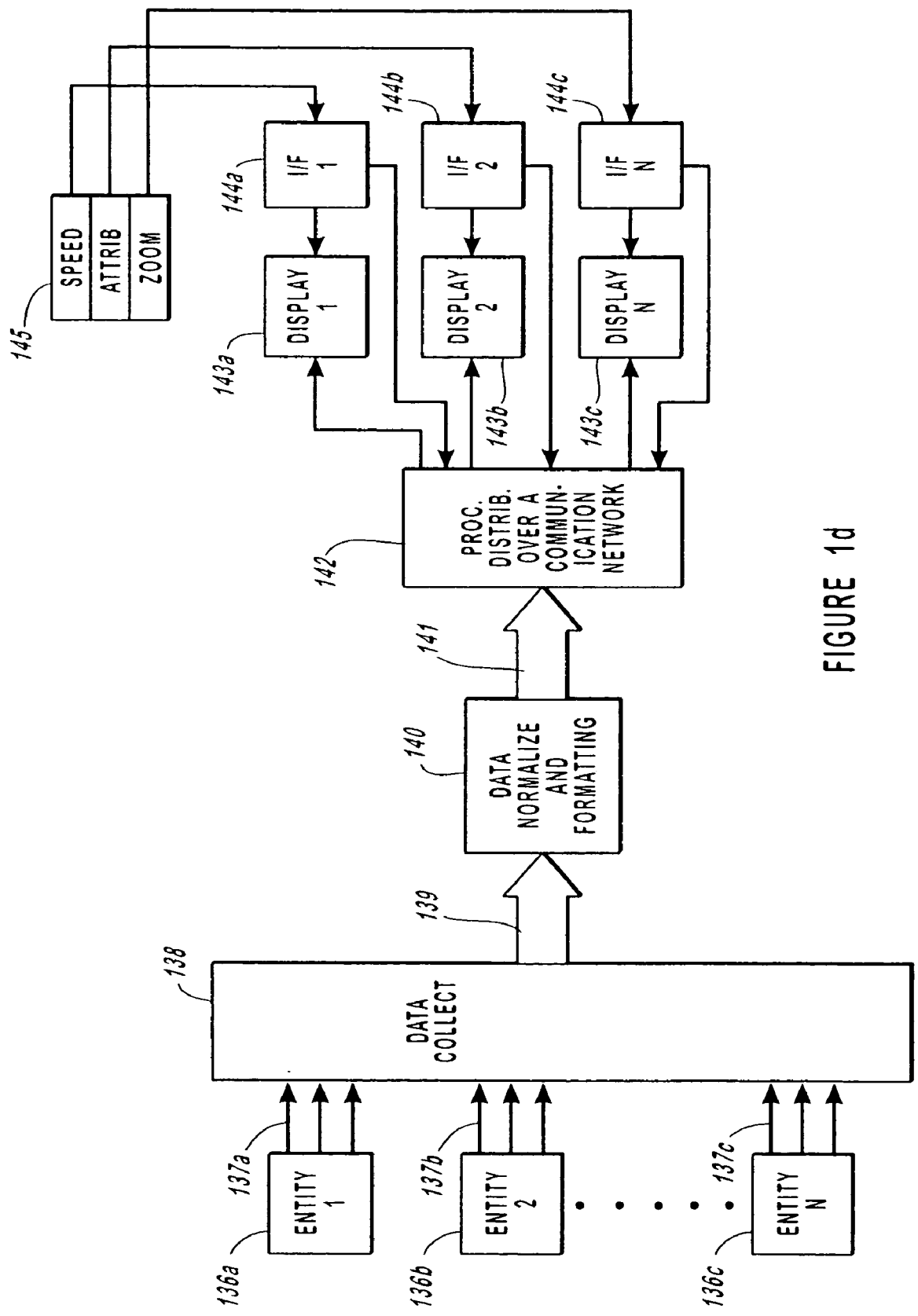
FIG. 1d is a top-level block diagram of a second preferred processing path of this invention.

FIG. 1d is a top-level block diagram of a second preferred processing path of this invention. In this embodiment of the invention a plurality of entities 136a,b,c are attached to sensors 137a,b,c which communicate sensor data to a data collection mechanism 138, which receives and organizes the sensed data. The data collection mechanism 138 is connected 139 to the data normalize and formatting process 140. The data normalize and formatting process 140 passes the normalized and formatted data 141 to the distributed processors 142. Typically and preferably the processing 142 is distributed over the Internet, although alternative communication networks may be substituted without departing from the concept of this invention. Each processing unit 142 is connected to any of the display devices 143a,b,c and receives command control from a user from a number of interface units 144a,b,c, each of which may also be connected directly to a display devices 143a,b,c. The interface units 144a,b,c receive commands 145 from the user that provide speed, zoom and other visual attributes controls to the displays 143a,b,c.

FIGS. 2a, 2b, 2c, and 2d are representative 3-D objects representing critical functions. Each 3-D object is provided as a symbol for a critical function of the entity whose health is being monitored. The symbol is created by selecting the interdependent variables that measure a particular physiologic function and expressing the variable in spatial (x,y,z) and other dimensions. Each 3-D object is built from 3-D object primitives (i.e., a cube, a sphere, a pyramid, a n-polygon prism, a cylinder, a slab, etc.). More specifically, the spatial dimensions (extensions X, Y and Z) are modeled after the most important physiologic variables based on (1) data interdependency relationships, (2) rate, type and magnitude of change in data flow, (3) geometric nature and perceptual potential of the 3-D object, for example a pyramid versus a cylinder, (4) potential of the object's volume to be a data-variable itself by modeling appropriate data into x, y and z dimensions (e.g., in one preferred application of the invention, cardiac output is the result of heart rate (x and y dimensions) and stroke volume (z)), (5) orthographic viewing potential (see viewport) and (6) the relationship with the normal values framework.

The first representative object 201, shown in FIG. 2a, is an engine process. The object 201 representing this process is provided on a standard x-y-z coordinate axis 202. The correlation between temperature, shown in the x1-dimension 204, engine RPM, shown in the y1-dimension 205 and exhaust gas volume, shown in the z1-dimension 203 is shown by changes in the overall sizes and proportion of the object 201. In the shown example object 201 the engine gas volume 203 is large, when RPM 205 is low and the engine temperature 204 is in the middle range. This combination of values, even without specific identified values suggests an engine's starting point.

The second representative object 206, shown in FIG. 2b, is an object representing cardiac function using stroke volume, in the y2-dimension 209, and the heart rate per second, shown as the x2, z2 dimensions. The total cardiac volume is shown as the total spherical volume 208.

The third representative object 211, shown in FIG. 2c, represents the interaction between the number of contracts, shown in the y3-dimension 212, the average revenue per contract, shown in the z3-dimension 214, and the average time per contract, shown in the x3-dimension 213. Assessing the interaction among these variables is important in monitoring of a sales department's operations.

The fourth representative object 215 is shown in FIG. 2d, shows the respiratory function generated by the respiratory rate, shown in x4-dimension 216, the respiratory volume, shown in the y4-dimension 216, and inhalation/exhalations, shown in the z4-dimension 218.

Figure 3:
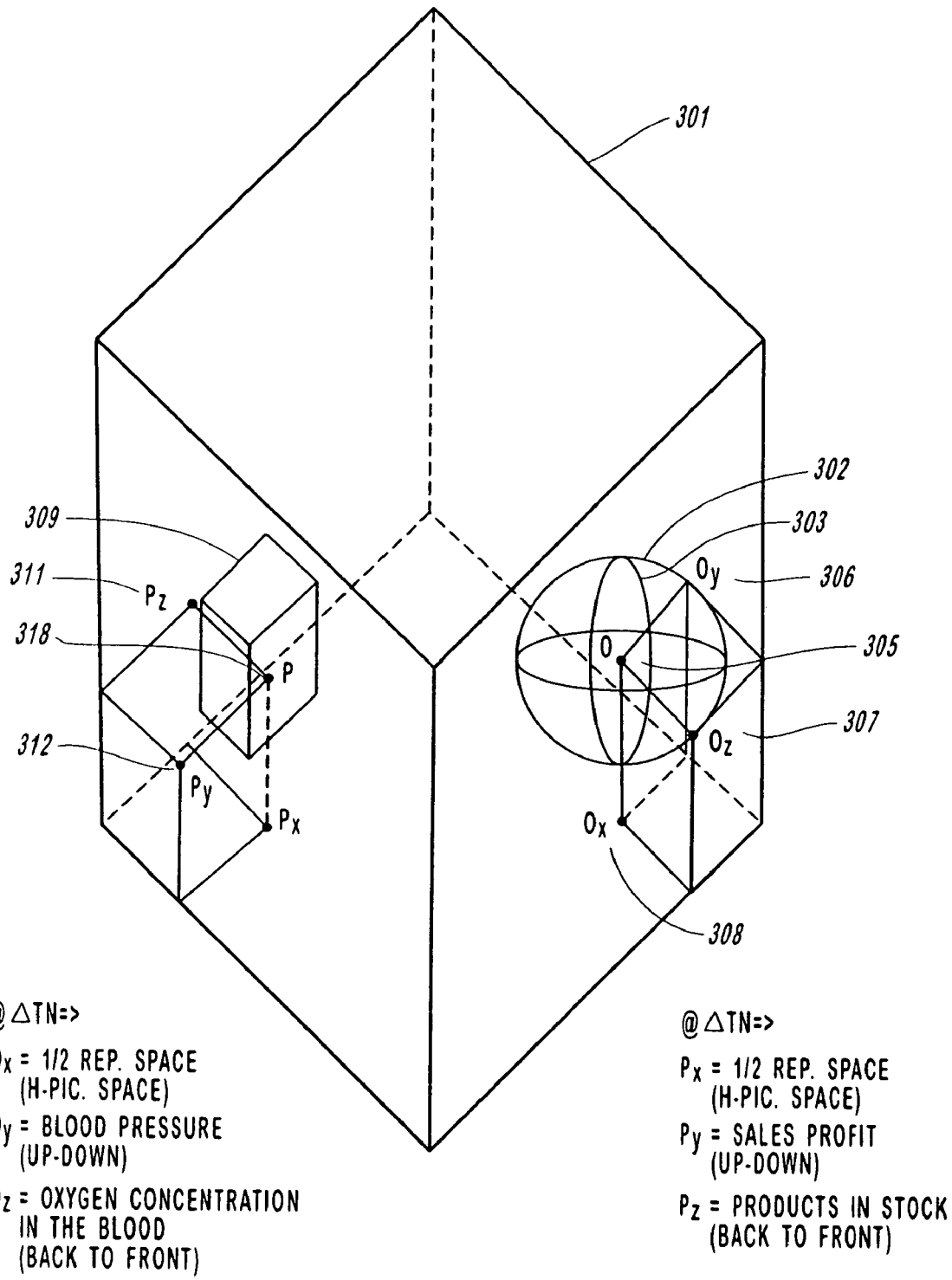
FIG. 3 is a representation of data objects in H-space.

FIG. 3 is a representation of data objects in H-space 301. Data sets are represented as 3-D objects of various characteristics and relationships within a 3-D representation space. The data representation environment in this figure is used to map the physiologic data in 3-D and is what is referred to as "Health-space" or "H-space" 301. The 3-D objects are placed within H-space on the 3 coordinates of their geometric centers. The coordinates for an object's geometric center depends on the relevant data associated to the particular critical function the object represents. For example, in the preferred embodiment, the cardiac function object, shown as a spherical object 302, is placed in H-space 301 based on Mean Blood Pressure, designated as Oy 306 and Oxygen Saturation in the Blood, shown as Oz 307. In the other example object, the prism 309 is placed in H-space 301 depending on sales profit, shown as Py 312, and products in stock, shown as Pz, 311. The location of 3-D objects in H-space 301 allows for the overall extension envelope of H-space, the relationship between 3-D objects and spaces within H-space 301, the viewport display areas and the departure from normative values. Typically and preferably the centers of the objects 302, 309 are located in the middle of the x-dimension of H-space 301.

Figure 4A:
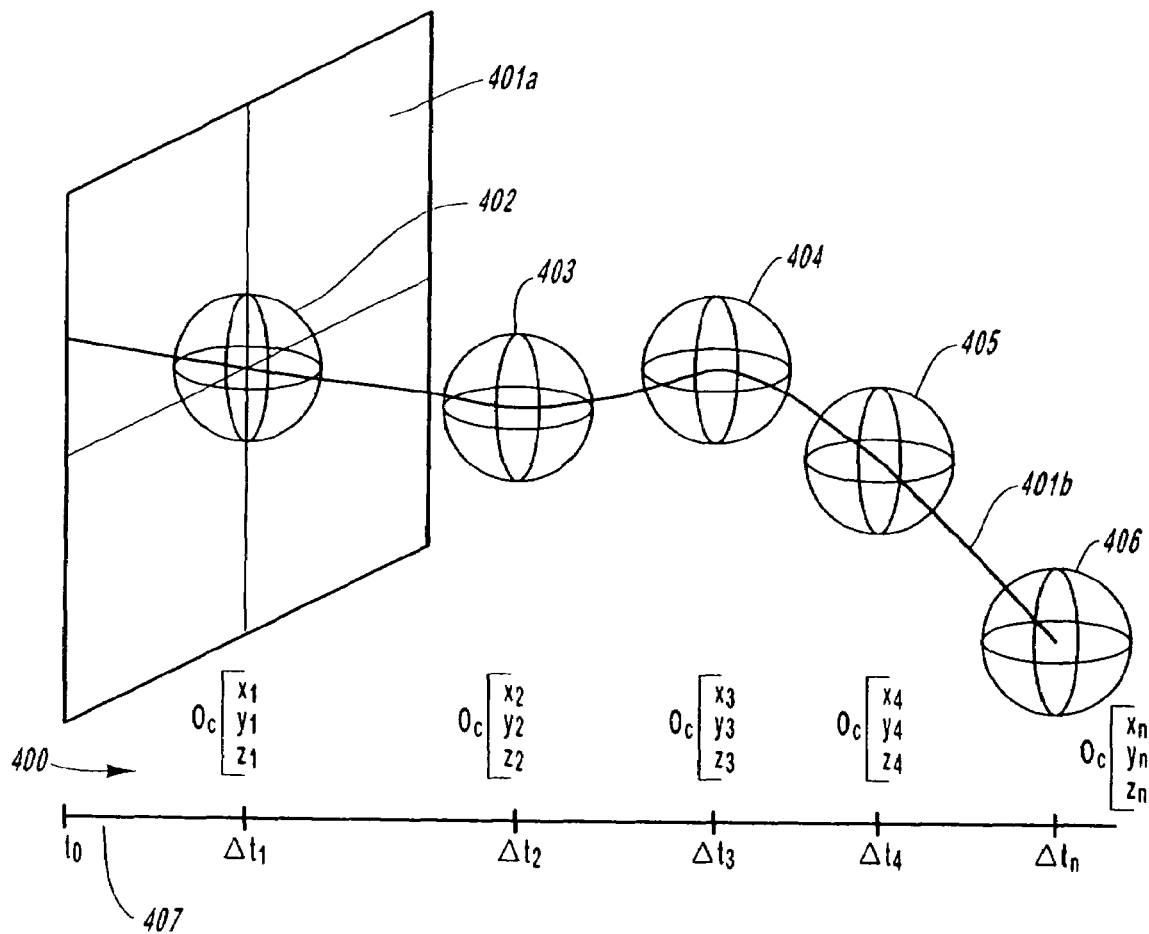
FIGS. 4a and 4b are representative views of changes in data objects in time.
Figure 4B:
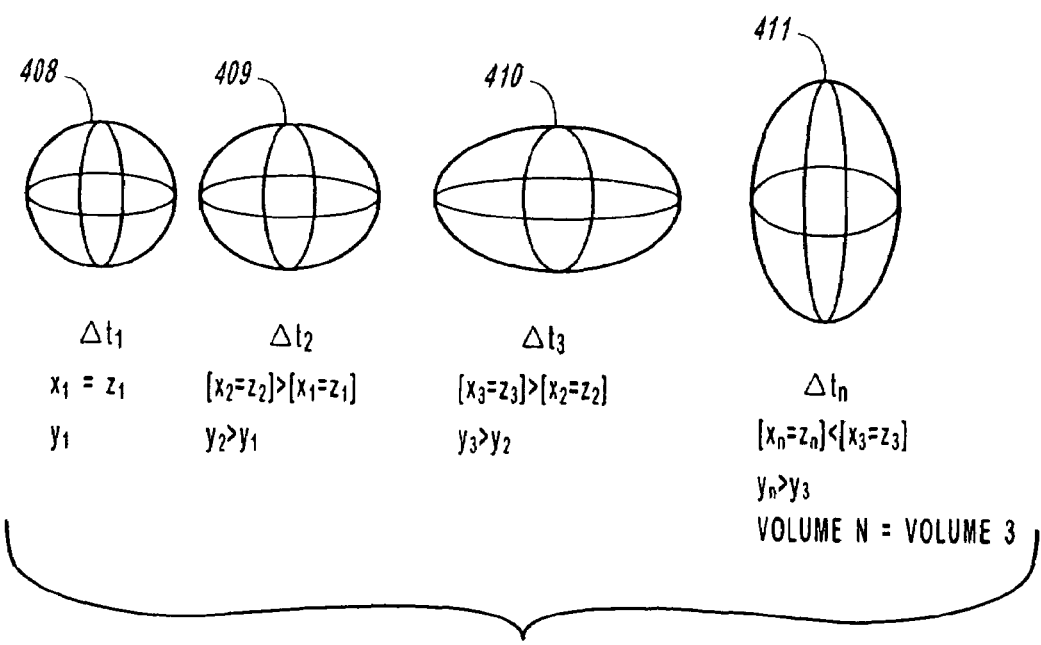

FIGS. 4a and 4b are representative views of changes in data objects in time. In FIG. 4a, the x-coordinate 400 is used to measure the temporal dimension of an objects 402 trajectory. The y-z plane 401a determines the location of an object's geometric center within H-space. Increases or decreases in data values associated with the coordinates of the object's geometric center that make that object's location change in time as shown in path line 401b. In this view, the object 402 is presented in four different time intervals 403, 404, 405, 406, thereby creating a historical trajectory. The time intervals at which the object 402 is shown are provided 407. In FIG. 4b, increases in size and proportion are presented, 408, 409, 410, 411 providing an example of changes in values. The monitoring of these changes in time assists the user establish and evaluate comparative relationships within and across H-states.

Figure 5A:
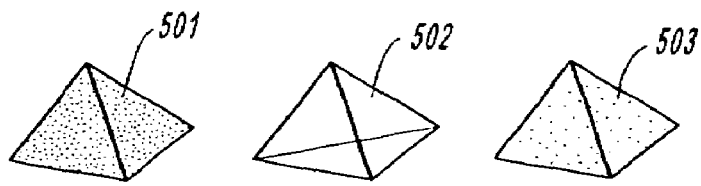
FIGS. 5a, 5b, 5c, 5d, 5e, 5f, 5g and 5h are representative views of properties of data objects provided in the preferred embodiment of this invention.
Figure 5B:
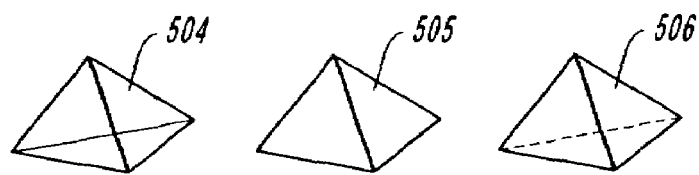
Figure 5C:
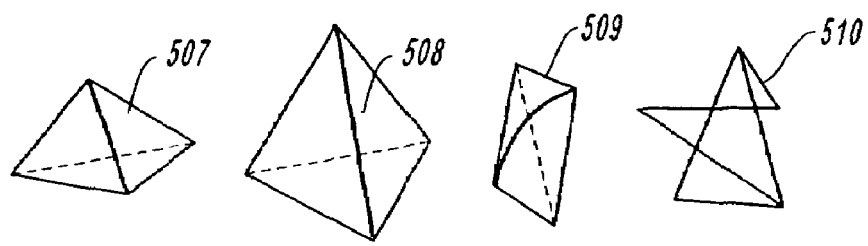
Figure 5D:
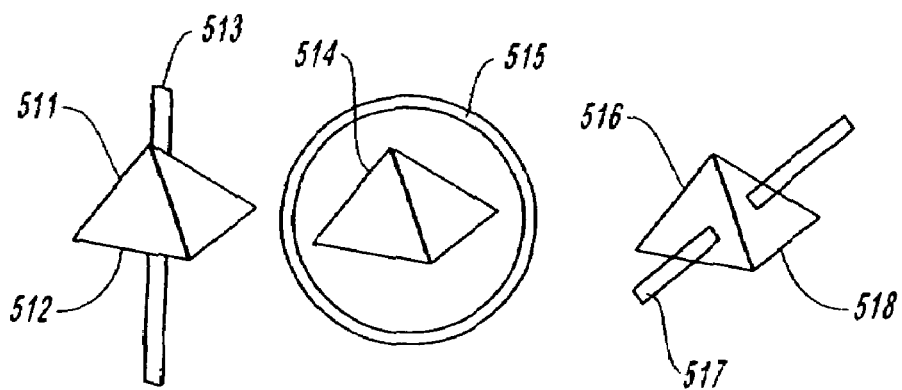
Figure 5E:
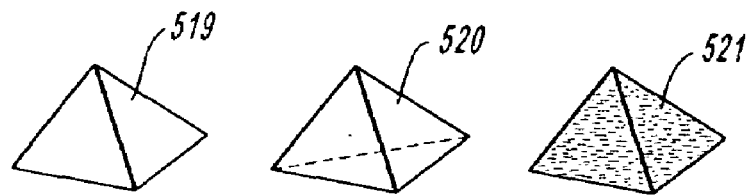
Figure 5F:
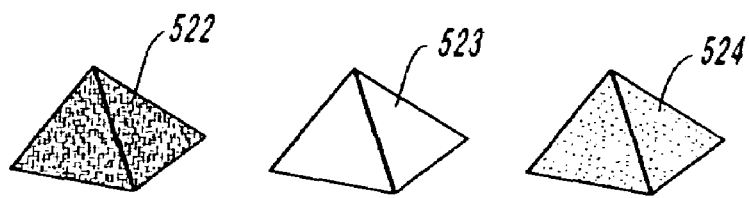
Figure 5G:
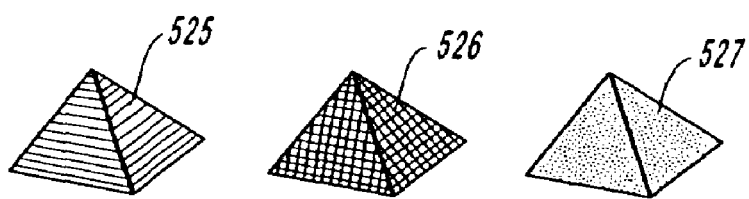
Figure 5H:
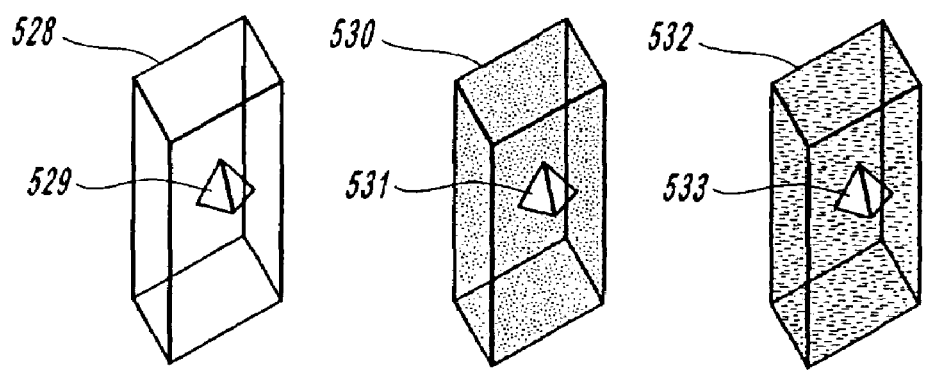

FIGS. 5a, 5b, 5c, 5d, 5e, 5f, 5g and 5h are representative views of properties of data objects provided in the preferred embodiment of this invention. In addition to the three x-y-z spatial dimensions used for value correlation and analysis, 3-D objects may present data value states by using other geometric, aesthetic, and aural attributes that provide for the mapping of more physiologic data. These figures show some of the representative other geometric, aesthetic, and aural attributes supported for data presentation in this invention. FIG. 5a shows changes in apparent volumetric density. A solid object 501 is shown in relation to a void object 502 and an intermediate state 503 object. FIG. 5b shows changes in apparent 3-D enclosure. An open object 504, a closed object 505, and an intermediate state 506 is shown. FIG. 5c shows the apparent degree of formal deformation. A normal object 507, a distorted object 508, a transformed object 509, and a destroyed object 510 are shown in comparison. FIG. 5d shows secondary forms of the objects. "Needles" 513 protruding through a standard object 512 in combination 511 is shown in comparison with a boundary 515 surrounding a standard object 514 and a bar 517 protruding into the original form object 518 forming a new combination object 516 are shown providing additional combination supported in this invention. FIG. 5e shows the various degrees of opacity of the object's surface, showing an opaque object 519, a transparent object 520 and an intermediate state object 521. FIG. 5f shows the various degrees of texture supported by the object display of this invention, including a textured object 522, a smooth object 523 and an intermediate textured object 524. FIG. 5g is intended to represent various color hue possibilities supported for objects in this invention. An object with color hue is represented 525 next to a value hue object 526 and a saturation hue object 527 for relative comparison. Naturally, in the actual display of this invention colors are used rather than simply the representation of color shown in FIG. 5g. FIG. 5h shows the atmospheric density of the representation space possible in the display of objects in this invention. An empty-clear space 528, a full-dark space 530 and an intermediate foggy space 523 are shown with 3-D objects shown within the representative space 529, 531, 533.

Aural properties supported in this invention include, but are not limited to pitch, timbre, tone and the like.

Figure 6:
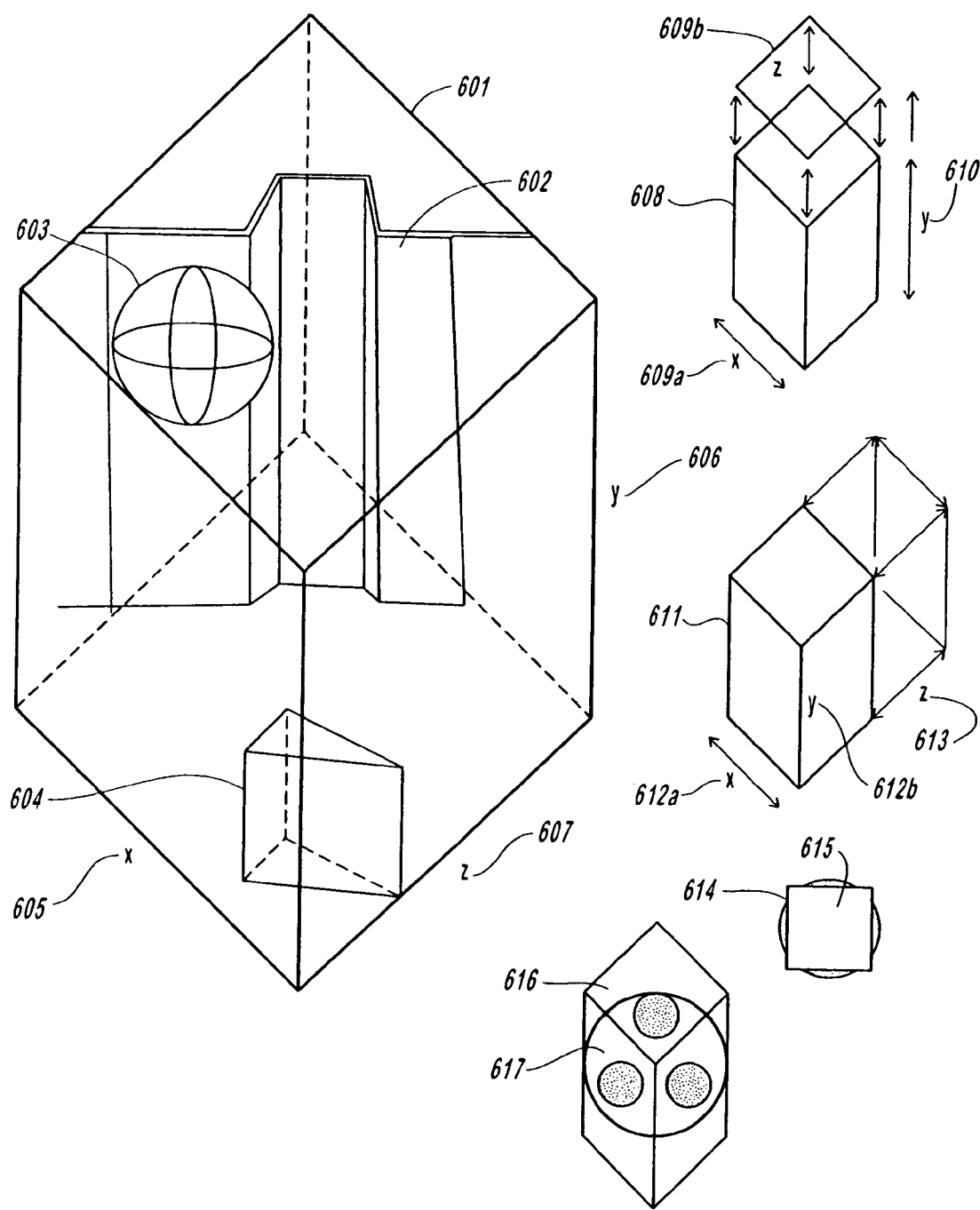
FIG. 6 shows a 3-D configuration of the objects in H-space in the preferred embodiment of the invention.

FIG. 6 shows the 3-D configuration of the objects in H-space in the preferred embodiment of the invention. In this view the local level, H-space 601 is shown within which the 3-D objects 602, 603, and 604 are located. Object 602 represents the respiratory function of an individual. Its 602 x-y-z dimensions change based on the parameter-based dimensional correlation. The object 603 represents the efficiency of the cardiac system by varying the x,y,z coordinates of the object. The object 604 represents a human brain function, also with the x,y,z dimensions changing based on the parameter-based dimensional correlation. In this way the user can easily view the relative relationships between the three physiological objects 602, 603, 604. Within H-space 601, the temporal coordinate (i.e., periodic time interval for data capturing that defines how H-space is plotted in Live-space—see FIG. 7) is a spatial dimension on which data is mapped. The x-dimension of 605 of the H-space 601 can be mapped to another independent variable such as heart rate period, blood pressure or the like. The location of an object in the y-dimension 606 of H-space 601 can be mapped to additional variables that are desired to be monitored such as SaO2 content, CaO2 content, or temperature in the blood. The location of an object in the z-dimension 607 of the H-space 601 can also be mapped to additional variables that the user desires to monitor. A hypothetical object 608 shows that the three coordinates are contextual to a particular object 608 and need not be the same for all objects, except in the object's 608 extension measuring properties. Fixed x- and z-dimension values 609a and 609b are shown as constant. The y-value 610 of this object 608 changes to fluctuating values or data type that results in the height of the object 608 increasing or decreasing. This view shows another object 611 showing the relationship between the three dimensions. Constant x- and y-values 612a and 612b are shown. The z-value 613 of this object 611 changes to fluctuating values or data types that result in the width of the object 611 increasing or decreasing. An overlapping view 614 of an object 615 that has extended past the H-space limitation. A limit of H-space 616 with a spherical object 617 located inside H-space 616 shown with the degree of extension shown in shaded circles.

Figure 7:
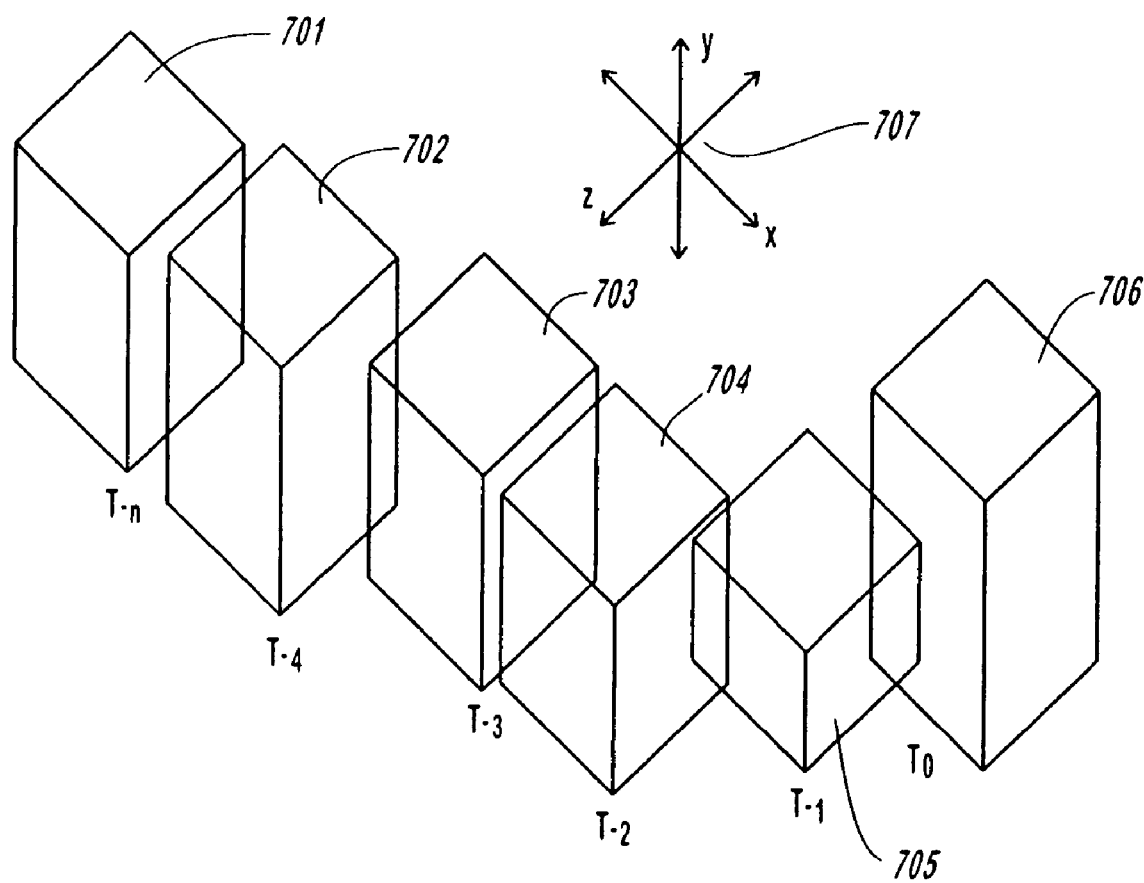
FIG. 7 shows H-space with a time coordinate along with local-space coordinates.

FIG. 7 shows a series of H-spaces 701, 702, 703, 704, 705, 706 along a global time coordinate 708, and the local-space coordinates 707 that governs each H-space. Each of these H-spaces represents progressive states of the dynamic system at pre-established temporal intervals ($T_0, T_{-1}, T_{-2}, \ldots T_{-n}$) and the six 701, 702, 703, 704, 705, 706 together show the evolution of that system over time, demonstrating the historical representation of individual H-states within an overall "Life-space" or "L-space." At the global level (or L-space), one of the coordinates, typically x, is always time. The temporal coordinate is scaled based on the intervals at which a particular functions system's physiologic data are collected by the art or as appropriate. This interval or module is fixed and constant across L-space and provides the necessary temporal frame of reference for comparing different H-spaces. The fixed temporal interval also determines the maximum x-extension of the representation envelope of H-space. The other two coordinates, y and z, provide L-space with extension and are not fixed. The three coordinates thus described provide a regulating 3-D environment within which the H-states can be visualized and related to each other.

Figure 8A:
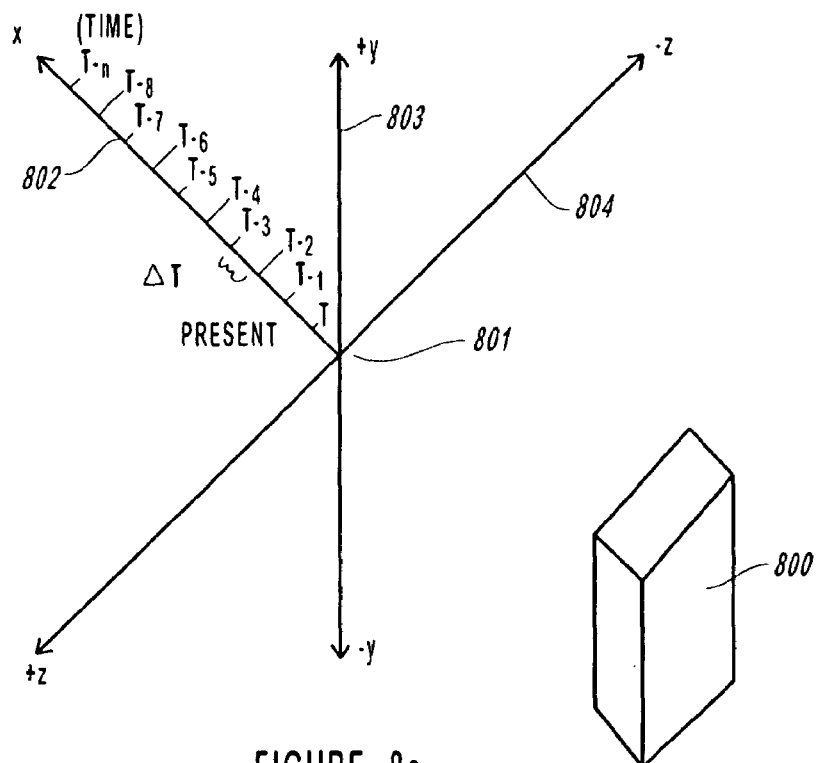
FIGS. 8a and 8b show the global level coordinate system of the preferred embodiment of this invention.
Figure 8B:
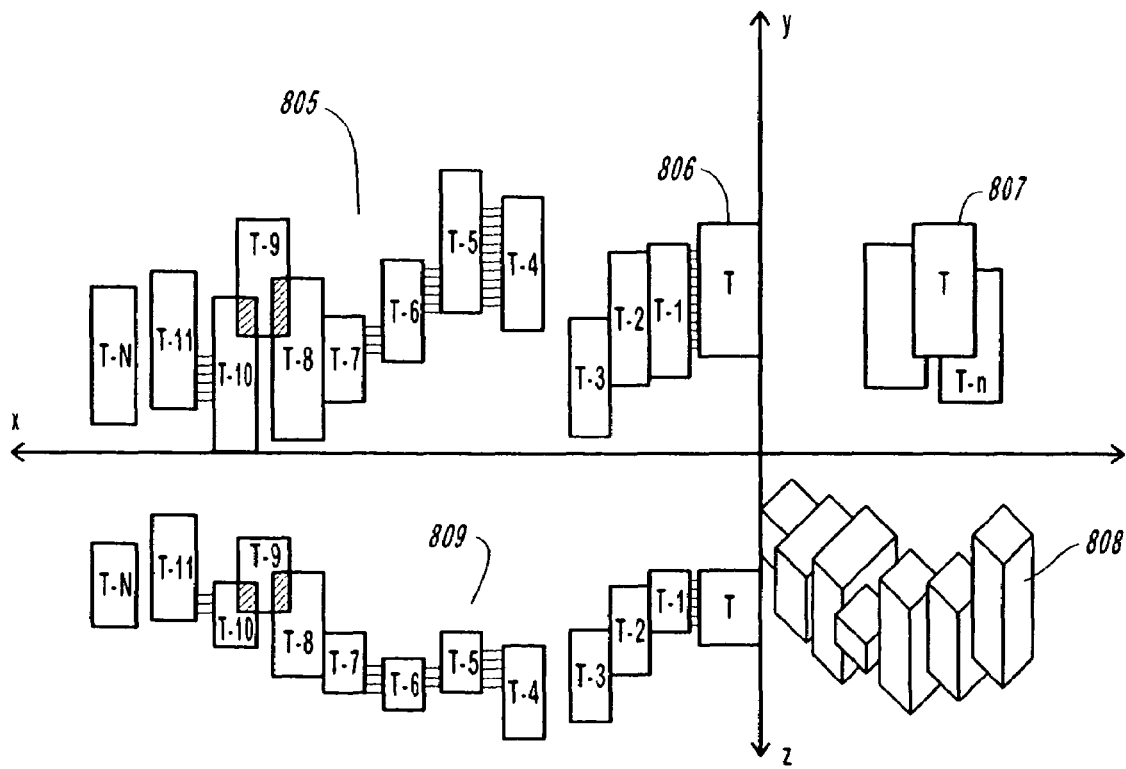

FIGS. 8a and 8b show the global level coordinate system of the preferred embodiment of this invention. FIG. 8a shows the L-space coordinate system 801 in its preferred embodiment. The x-dimension 802 of L-space is mapped to a constant time interval, set by means standard in the art or otherwise as appropriate. The present position of H-state is also indicated on the x-dimension 802. The y-dimension 803 in both positive and negative extensions is measured, up and down from the x-axis. This dimension 803 can be mapped to a data variable within particular 3D object in space. The z-dimension 804 is shown in both positive and negative extensions measured forwards and backwards from the intersecting x-axis. This dimension 804 can be mapped to a data variable within a particular 3D object in space. Now for FIG. 8b a prismatic object 800 represents a critical function, whose evolution is being monitored in L-space, of a given dynamic system. The front view 805 shows the different H-states of the prism/function 800 using a time T to T-n historical trend. The level of intersection and separation between the front views of the prism indicate abnormal health states of the critical function the object 800 represents. No separation or intersection shows normal function conditions. The trajectory in the y-dimension of the prism (i.e., H-states of the critical function) are mapped to a variable that cause their relative position to change in the+ and −y dimension. The current state 806 of the prism is shown in this front view 805. A top view of 809 of the three-dimensional L-space is shown, showing the evolution of the prism 800 backward in time and showing a T to T-N historical trend. The level of intersection and separation indicate abnormal health states of the particular critical function the prism represents. No separation or intersection shows normal conditions. The trajectory in the z-dimension of the object is mapped to a variable that causes their position to change in the+ and −z dimension. This top view shows both the z and y trajectories in one comprehensive view. The perspective view 808 of L-space gives a comprehensive view of the interaction of the prisms (the H-states of the function) and their movement in all dimensions. The side view 807 of L-space shows the prisms and their positions in L-space giving a simultaneous view of z and y trajectories.

Figure 9A:
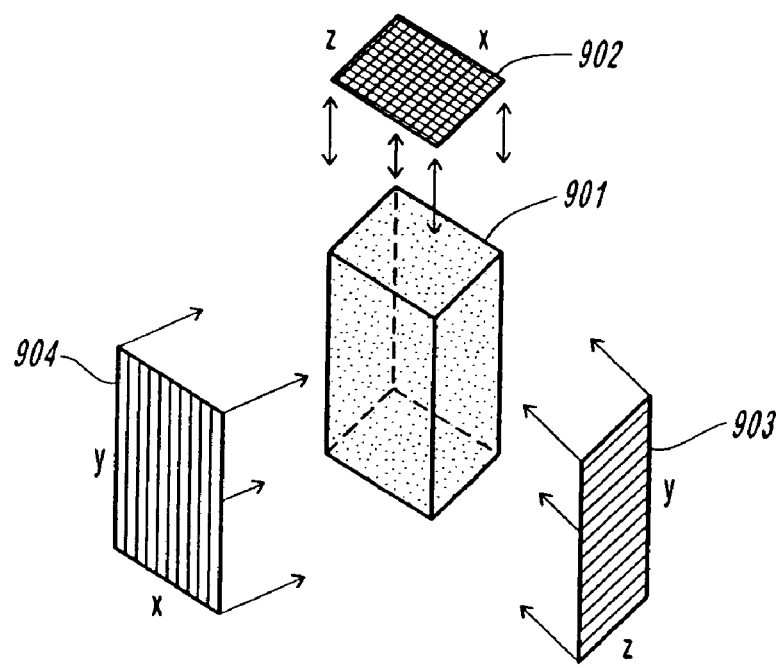
FIGS. 9a and 9b show various viewpoints of the data within H-space in the preferred embodiment of this invention.
Figure 9B:
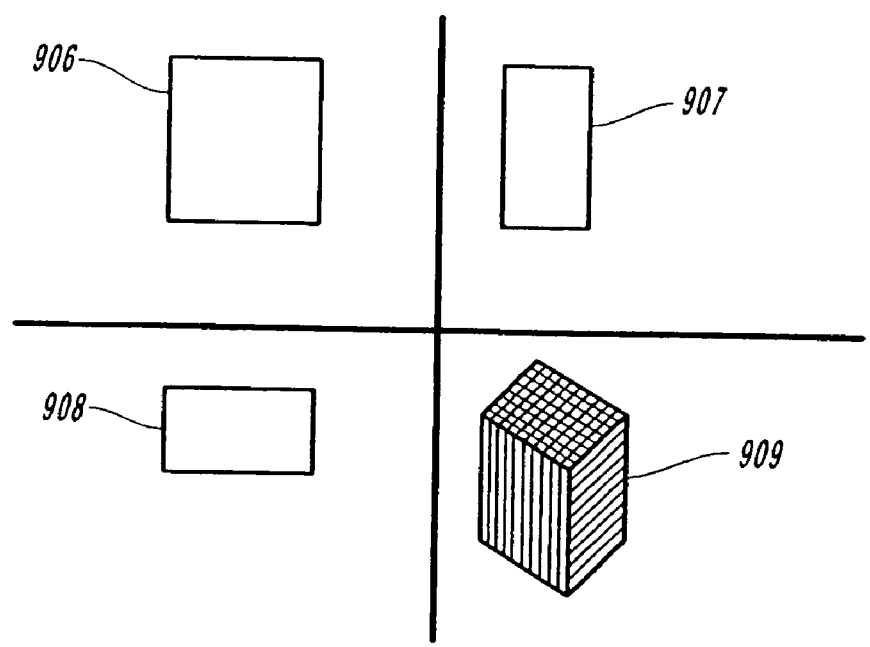

FIGS. 9a and 9b shows various viewpoints in which the data may be visualized in the preferred embodiment of this invention. This figure shows representations of a data object (a prism) and is provided to show that there are two basic types of viewports: orthographic and perspectival. The orthographic viewports 906, 907, 908, of FIG. 9b use a parallel system of projection to generate representations of H-space that maintains dimensional constancy without deformation. Some examples of orthographic views include traditional architectural or engineering views of objects, such as a top view, a front view, and a side view. The orthographic viewport allows for accurate and focused 2-D expressions of the actual 3-D object. The perspectival viewport 909, shown in FIG. 9b uses a focal system of projection to generate depictions analogous to our perception of reality but at the cost of deformation and lack of dimensional constancy. For example, the top view 902 along with the side view 903 and the front view of 904 of the 3-D data object 901 are shown in FIG. 9a. FIG. 9b shows three orthogonal views 906, 907, 908 along with a perspective view 909 of the current data object. The number and types of viewports used in a particular embodiment of the invention may range from one type, for example a perspective viewport allowing immerse virtual reality, to combinations of both types. In the preferred current embodiment, there are the four viewports shown in FIG. 9b. Given the 3-D nature of data objects and H-space, viewports provide the user with different depictions of the same data.

Figure 10:
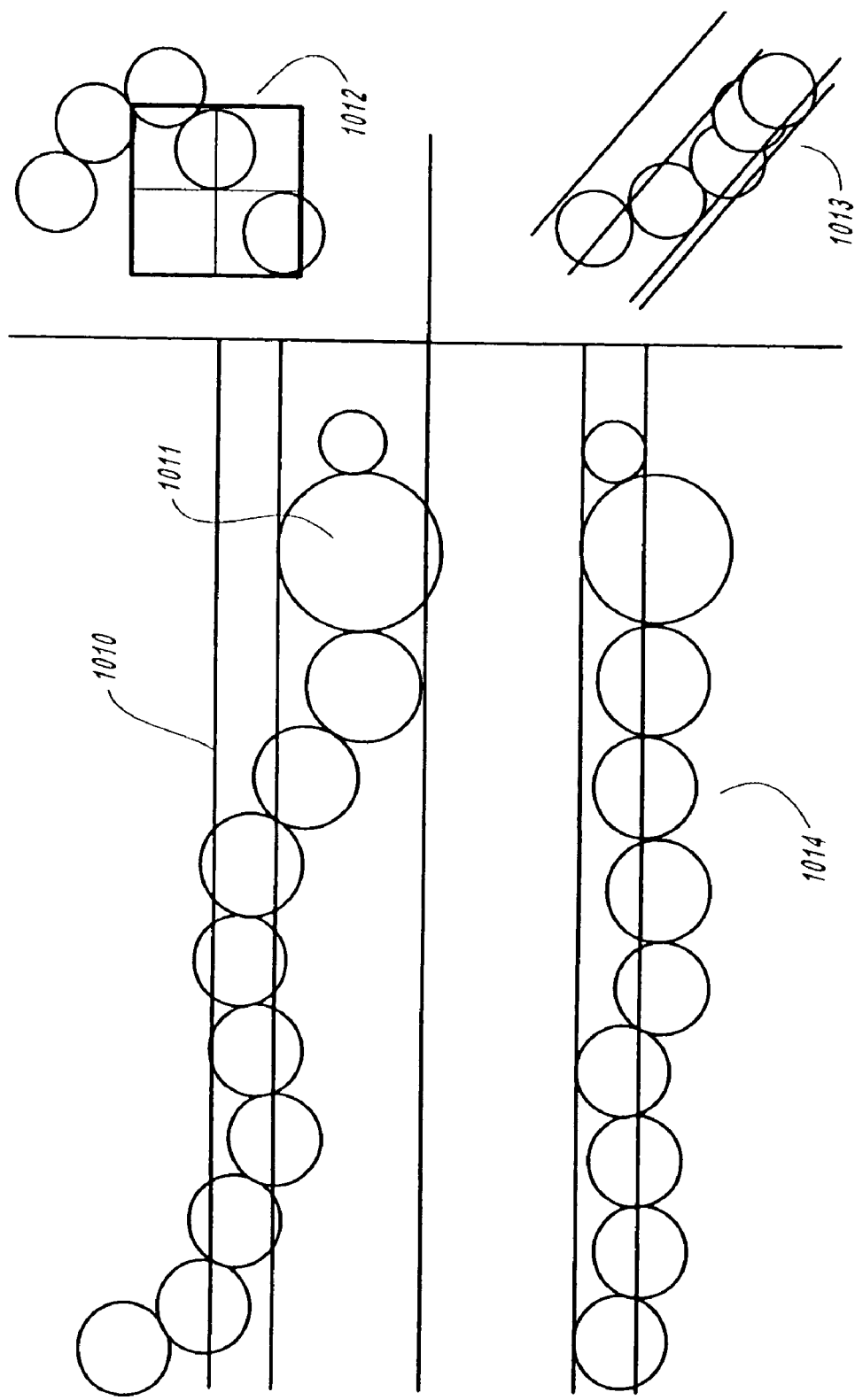
FIG. 10 shows the transformation of an object in space in context, with a reference framework, in the preferred embodiment of this invention.

FIG. 10 shows the transform of an object in space in context, with a reference framework, in the preferred embodiment of this invention. The referential framework 1010 is typically set based on population normals or patient normals. This framework assists the user to see deviations from normal very quickly. An individual spherical object 1011 that represents cardiac function is shown located in L-space and in relation to the referential framework. A side view 1012 is shown along with several cardiac objects. In this view the referential framework provides a center target point so that a user can make the necessary corrections to bring the object back to the ideal center of the framework. A perspectival view 1013 of the framework is also shown along with several cardiac objects. The top view 1014 of the framework is shown with several spherical objects (representing cardiac states). This figure demonstrates the variety of viewports provided to the user by this invention, which provides enhanced flexibility of analysis of the displayed data.

Figure 11A:
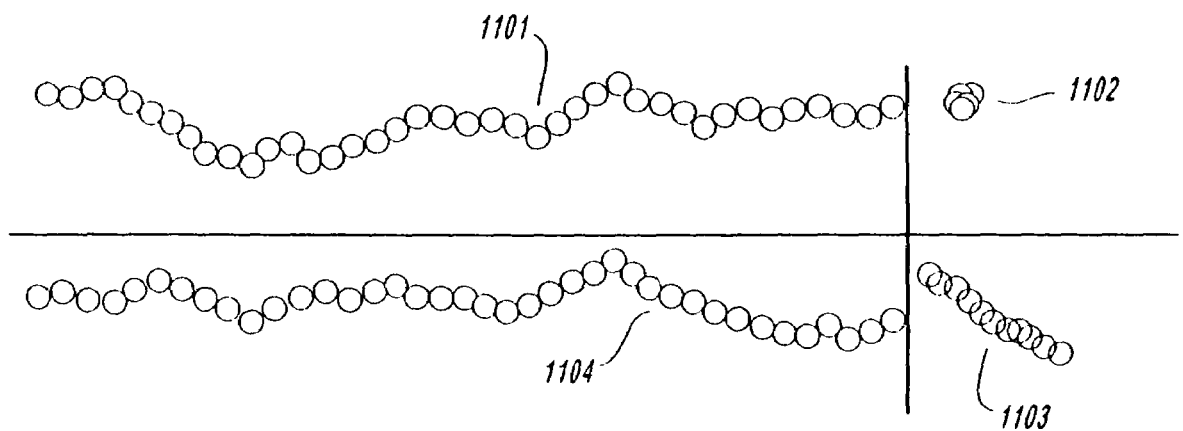
FIG. 11a shows the zooming out function in the invention.

FIG. 11a shows the zooming out function in the invention. This invention provides a variety of data display functions. This figure shows the way views may be zoomed in and out providing the relative expansion or compression of the time coordinate. Zooming out 1101 permits the user to look at the evolution of the system's health as it implies the relative diminution of H-states and the expansion of L-space. This view 1101 shows a zoomed out view of the front view showing a historical view of many health states. A side view 1102 zoomed out view is provided to show the historical trend stacking up behind the current view. A 3-D perspectival, zoomed out view 1103 showing the interaction of H-states over a significant amount of time is provided. A zoomed out top view 1104 shows the interaction of H-states over a large amount of time.

Figure 11B:
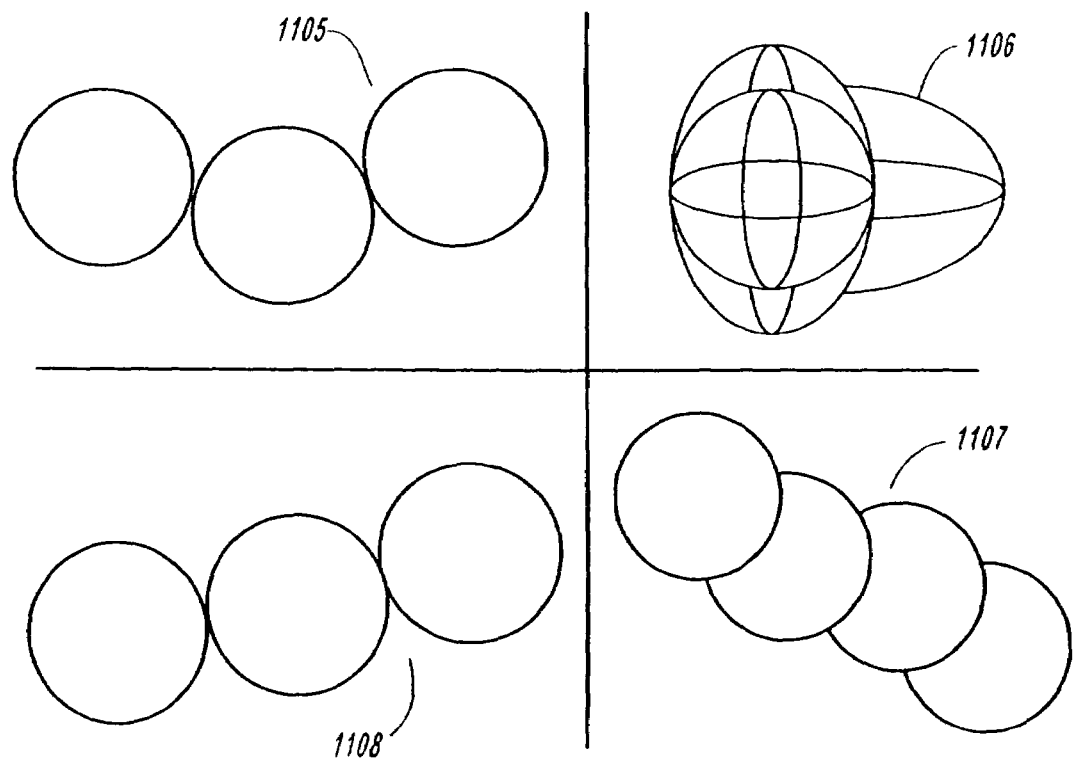
FIG. 11b shows the zooming in function in the invention.

FIG. 11*b* shows the zooming in function of the invention. The zooming in front view 1105 is shown providing an example of how zooming in permits a user to focus in on one or a few H-states to closely study specific data to determine with precision to the forces acting on a particular H-state. A zoomed in side view 1106 is provided showing the details of specific variables and their interactions. A zoomed in 3-D perspective view 1107 of a few objects is also shown. Also shown is a zoomed in top view 1108 showing the details of specific variables and their interaction.

Figure 12A:
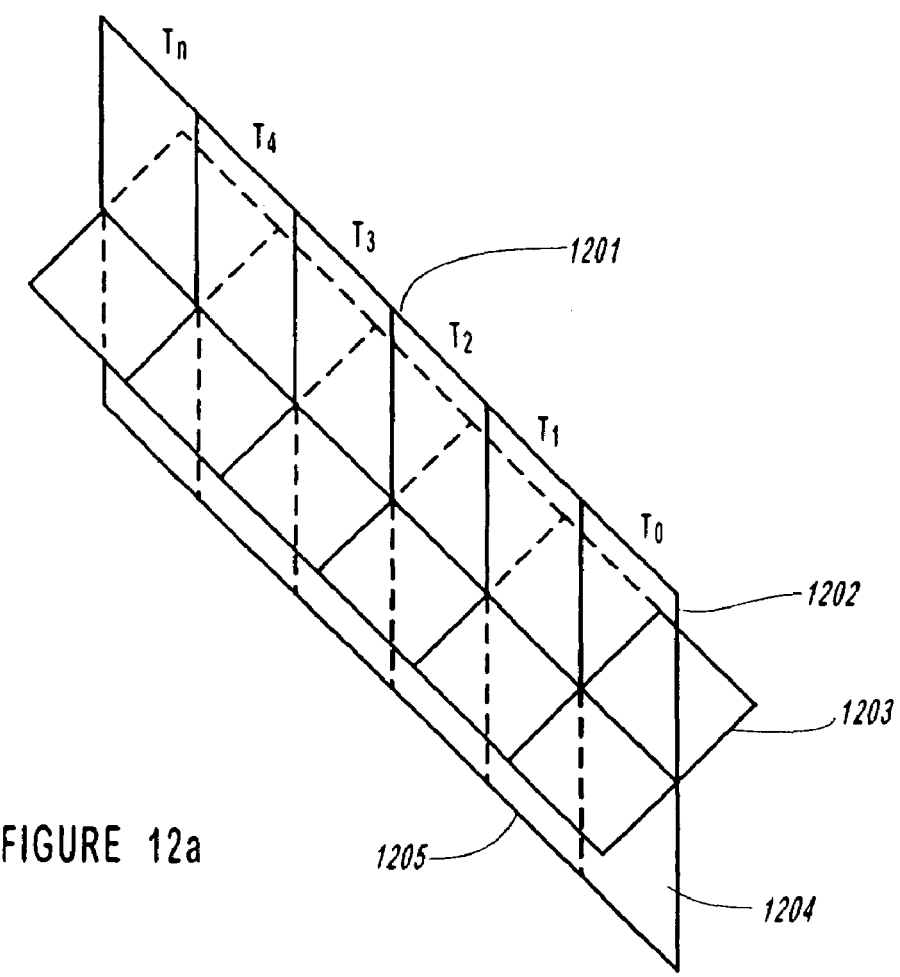
FIGS. 12a and 12b show a 3-D referential framework of normative values.
Figure 12B:
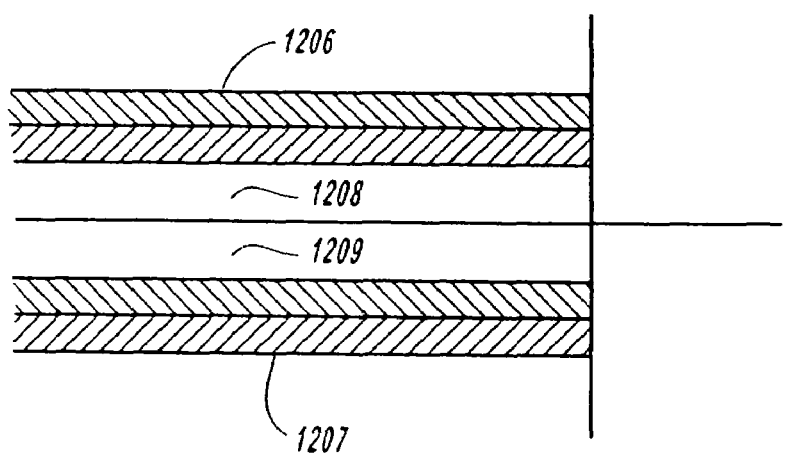

FIGS. 12*a* shows a 3-D referential framework of normative values that is provided to permit the user a direct comparison between existing and normative health states, thereby allowing rapid detection of abnormal states. The reference framework 1201 works at both the global L-space level and the local H-space level. "Normal" values are established based on average historical behavior of a wide population of systems similar to the one whose health is being monitored. This normal value constitutes the initial or by-default ideal value, which, if necessary may be adjusted to acknowledge the particular characteristics of a specific system or to follow user-determined specifications. The highest normal value of vital sign "A" 1202 (+y) is shown, along with the lowest normal value of "B" 1203 (−z), the lowest normal value of vital sign "A" 1204 (−y) and the highest normal value of vital sign "B" 1205 (+z). In FIG. 12*b*, abnormal values of "A" and "B" are shown in an orthogonal view. An abnormally high value of "A" 1206, an abnormally low value of "B" 1207, an abnormally low value of "A" 1208 and an abnormally high value of "B" 1209 are shown.

FIG. 13 shows a comparison of the interface modes of the preferred embodiment of this invention. This invention provides two basic types of interface modes: (a) standardized or constrained customization; and (b) free or total customization. Each is directed toward different types of applications. The standardized or constrained customization 1301 uses a method and apparatus for user interface that is set a-priori by the designer and allows little customization. This interface mode establishes a stable, common, and standard symbolic system and displaying method that is "user-resistant". The fundamental rules, parameters, structure, time intervals, and overall design of L-space and H-space are not customizable. Such a normalized symbolic organization creates a common interpretative ground upon which different users may arrive at similar conclusions when provided common or similar health conditions. This is provided because similar data flows will generate similar visualization patterns within a standardized symbolic system. This interface method is intended for social disciplines, such as medicine in which common and agreeable interpretations of the data are highly sought after to ensure appropriate and verifiable monitoring, diagnosis and treatment of health states. The customization permitted in this mode is minimal and is never threatening to render the monitoring device incomprehensible to other users.

The free or total customization interface mode 1302 provides a symbolic system and displaying method that is changeable according to the user's individual needs and interests. Although the invention comes with a default symbolic L-space and H-space, its rules, parameters, structure, time intervals, and overall design are customizable. This interface mode also permits the user to select what information the user wishes to view as well as how the user wishes to display it. This interface mode may produce personalized displays that are incomprehensible to other users, but provides flexibility that is highly desired in individual or competitive pursuits that do not require agreeable or verifiable interpretations. Examples of appropriate applications may include the stock market and corporate health data monitoring.

Figure 14:
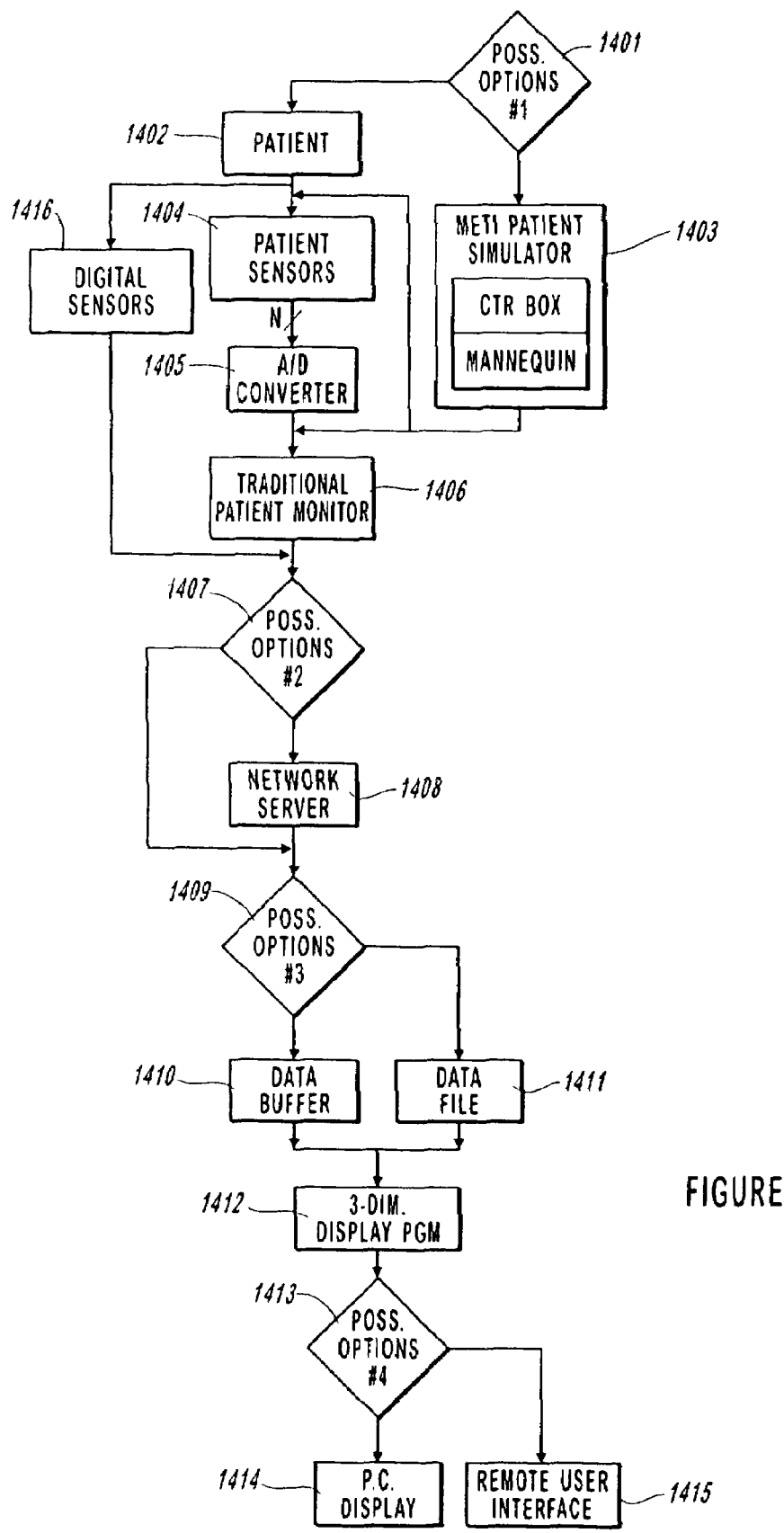
FIG. 14 is a hardware system flow diagram showing various hardware components of the preferred embodiments of the invention.

FIG. 14 is a hardware system flow diagram showing various hardware components of the preferred embodiments of the invention in a "natural system" medical application. Initially a decision 1401 is made as to the option of using data monitored on a "real" system, that is a real patient, or data from the simulator, for anesthesiology training purposes. If the data is from a real patient, then the patient 1402 is provided with patient sensors 1404, which are used to collect physiological data. Various types of sensors, including but not limited to non-invasive BP sensors, ECG leads, SaO2 sensors and the like may be used. Digital sensors 1416 may also provide physiological data. An A/D converter 1405, is provided in the interface box, which receives the analog sensor signals and outputs digital data to a traditional patient monitor 1406. If the data is produced 1401 by the simulator 1403, a control box and mannequins are used. The control box controls the scenarios simulated and the setup values of each physiological variable. The mannequins generate the physiological data that simulates real patient data and doctors collect the data through different, but comparable sensors. The traditional patient monitor 1406 displays the physiological data from the interface box on the screen. Typically and preferably, this monitor 1406 is the monitor used generally in an ICU. A test 1407 is made to determine the option of where the computations and user interface are made, that is whether they are made on the network server 1408 or otherwise. If a network server 1408 is used, all or part of the data collection and computation may be performed on this computer server 1408. An option 1409 is proved for running a real time representation versus a representation delayed or replayed from events that previously occurred. For real time operation, a data buffer 1410 is provided to cache the data so that the representation is played in real time. For the replay of previous events, a data file 1411 provides the means for permanently storing the data so that visualization is replayed. The visualization software 1412 runs on a personal computer and can display on its monitor or on remote displays via the internet or other networking mechanism. Typically the physiological data measured on either a real patient or the simulator are fed to the personal computer from the traditional data monitor. A standard interface such as RS232, the Internet, or via a server, which receives data from the monitor, may serve as the communication channel to the personal computer running the visualization software 1412. This program 1412 is the heart of the invention. The program 1412 computes the representation and processes the user interface. An option 1413 is provided for computing and user interface on the local desktop personal computer or for distribution across the Internet or other network mechanism. If a local desktop personal computer is selected, the personal computer 1414 with an adequate display for computation of the visualization and user interface is provided. If a remote user interface 1415 is selected the display and user interface is communicated across the Internet.

Figure 15:
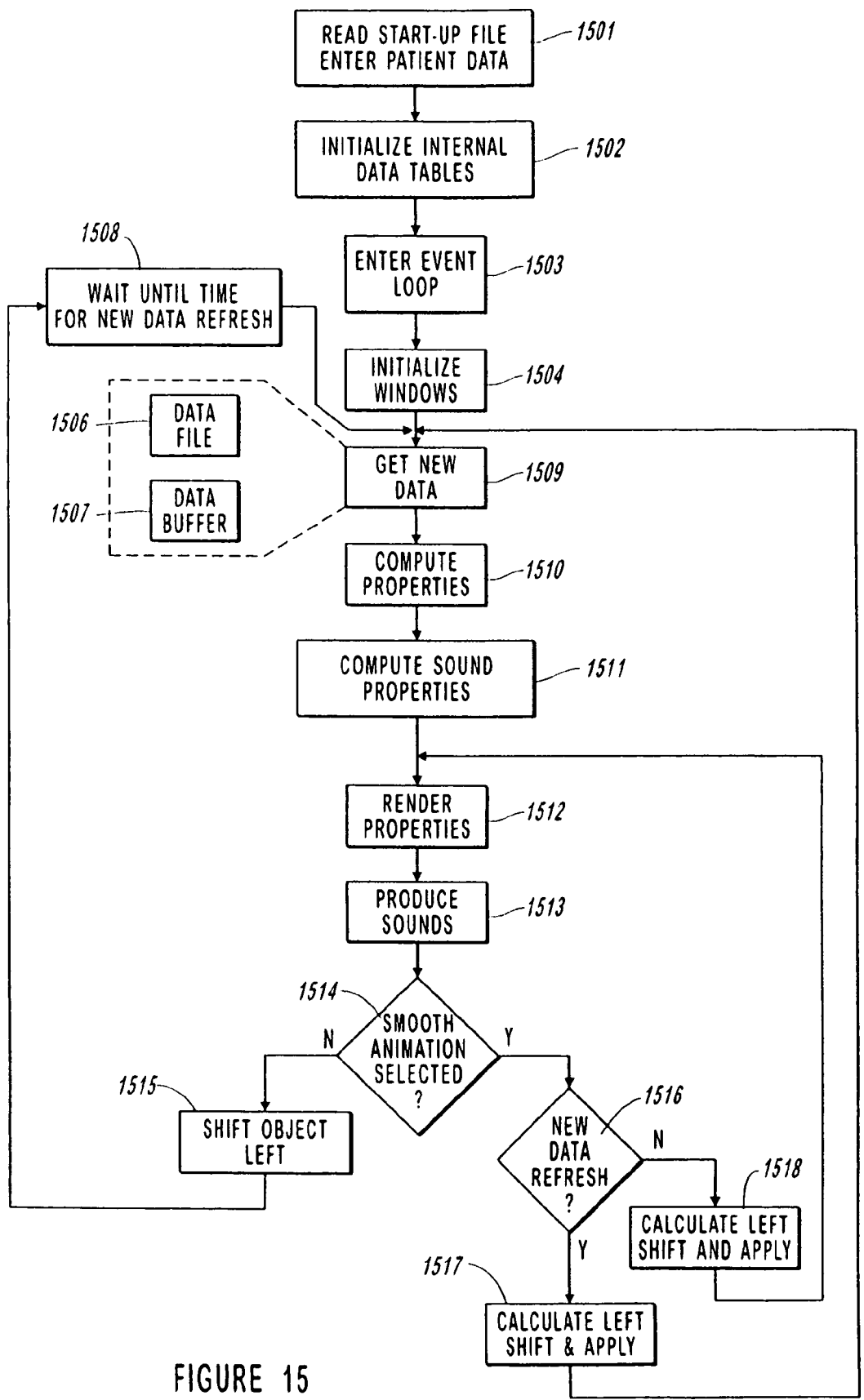
FIG. 15 is a software flow chart showing the logic steps of a preferred embodiment of the invention.

FIG. 15 is a software flow chart showing the logic steps of a preferred embodiment of the invention. The preferred embodiment of this invention begins by reading the startup file 1501, which contains the name of the window and the properties associated with the invention. The properties associated with the a window include formulas to set object properties, text that is to be rendered in the scene, the initial size of the window, the initial rotation in each window, zoom, lighting and patient data that describes the normal state of each variable. Internal data tables are next initialized 1502. For each new window encountered in the startup file a new window object is made and this window object is appended to the list of windows. The window object contains an uninitialized list of properties describing the state of the window, which is filled with data from the startup file. The event loop is entered 1503. This is a window system dependent infinite loop from which the program does not exit. After some initialization, the program waits for user input and then acts on this input. The program then takes control of the event loop for continuous rendering that is if there is no interactivity in the program. Initialization 1504 of windows is next performed. This involves calls to the window system dependent functions (these are functions that are usually different on different computational platforms) that creates the windows and displays them on the computer screen. In the current preferred embodiment of the invention, OpenGL is required, although alternative embodiments using other 3D application programming interfaces, such as PEX or DirectX, could be substituted without departing from the concept of this invention. Also, in the preferred embodiment of this invention, a personal computer graphics card is preferred in the personal computer so as to permit smooth animation with multiple windows. Although the lack of such a card is not absolutely required for operation of this invention. New data is received 1509, typically from the data file 1506 or the data buffer 1507. This new data 1509 can come from any source that generates floating-point numbers. The preferred line of data is composed of columns of floating point numbers separated by space. At this point the current time is also stored so that the next line of data can be obtained at the next user defined time interval, which is typically set at about 1 second. Object properties are next computed 1510. This is performed by using formulas that are specified in the startup file to compute properties of objects. Data fields in the formulas are specified by writing the column number preceded by a dollar sign. For example, $1/20.0 would divide the first field by 20.0. The specific properties in this application are: cardiac object dimensions, material properties, and position. Material properties can include the red, green, and blue components as they appear under ambient, diffuse, and specular light, as well as transparency. The cardiac object position includes the y and z positions as well as an x shift. If four or more lines of data have been acquired, the respiratory object properties are computed. A delay is necessary because a cubic spline is fitted, using four data points to do the fit, to the data points to generate a smooth respiratory object. Therefore, until four time steps have passed, the curtain is not rendered. Thereafter, it is rendered every time new data is acquired. Cardiac object properties include material properties and the height of the color bands. Blood pressure object length and materials are the thin cylinders that go through the top and bottom of each ellipsoid. Next, reference grid properties are computed. All objects, except the cardiac object reference are stationary, in the current implementation. The cardiac object reference can move according to the movement of the cardiac object if the user specifies this movement in the startup file. Next, sounds are computed 1511 and made audible 1513. Objects and reference grids are rendered 1512. Before rotation the newest object appears at the right side of the screen and oldest object is at the left side of the screen. Sound is produced 1513 next. A test 1514 is next made to determine if smooth animation is selected. If smooth animation is selected the scene will scroll during the time the program is waiting to get new data. The program, using available computing resources, selects the minimum time increment so that the shift of the objects can be rendered within the increment, but limiting the increment to the smallest increment that human eyes can detect. If smooth animation is not selected, objects are shifted to the left 1515 such that the distance from the center of the newest cardiac object to that of the former cardiac object is equal to the inter-cardiac spacing. The process waits 1508 until the current time minus the time since data was last obtained equals the data acquisition period specified by the user. If the current time minus the time when the data was last acquired equals the user specified data acquisition period then a new line of data is acquired. If smooth animation is selected, then the cardiac objects are shifted to the left by computing 1516 to that when it is time to get the next line of data, the cardiac objects have moved 1517, 1518 such that the distance from the rightmost cardiac object to the position where the new cardiac object will appear is equal to the inter-cardiac-object distance. For example, if it takes 0.20 seconds to render the previous scene, the period of data acquisition is 1.0 seconds, and the x shift of the rightmost cardiac object is 0.1 units then the program will shift the scene left (0.20/(1.0+0.20)*(1.0−0.1)=0.15. The formula in the denominator is (1.0+0.20 instead of 0.8 because, if the scene has been shifted left such that, when new data is acquired, the shifting has stopped (because the position of the cardiac objects satisfies the criteria that the distance from the center of the rightmost cardiac object to the center point where the new cardiac object will be rendered=1 unit) then the animation will no longer be smooth, that is, when new data is acquired the animation will appear to stop. Note, that the respiratory object is never entirely smoothly shifted because no data is available to render the object at the intermediate time steps.

Figure 16:
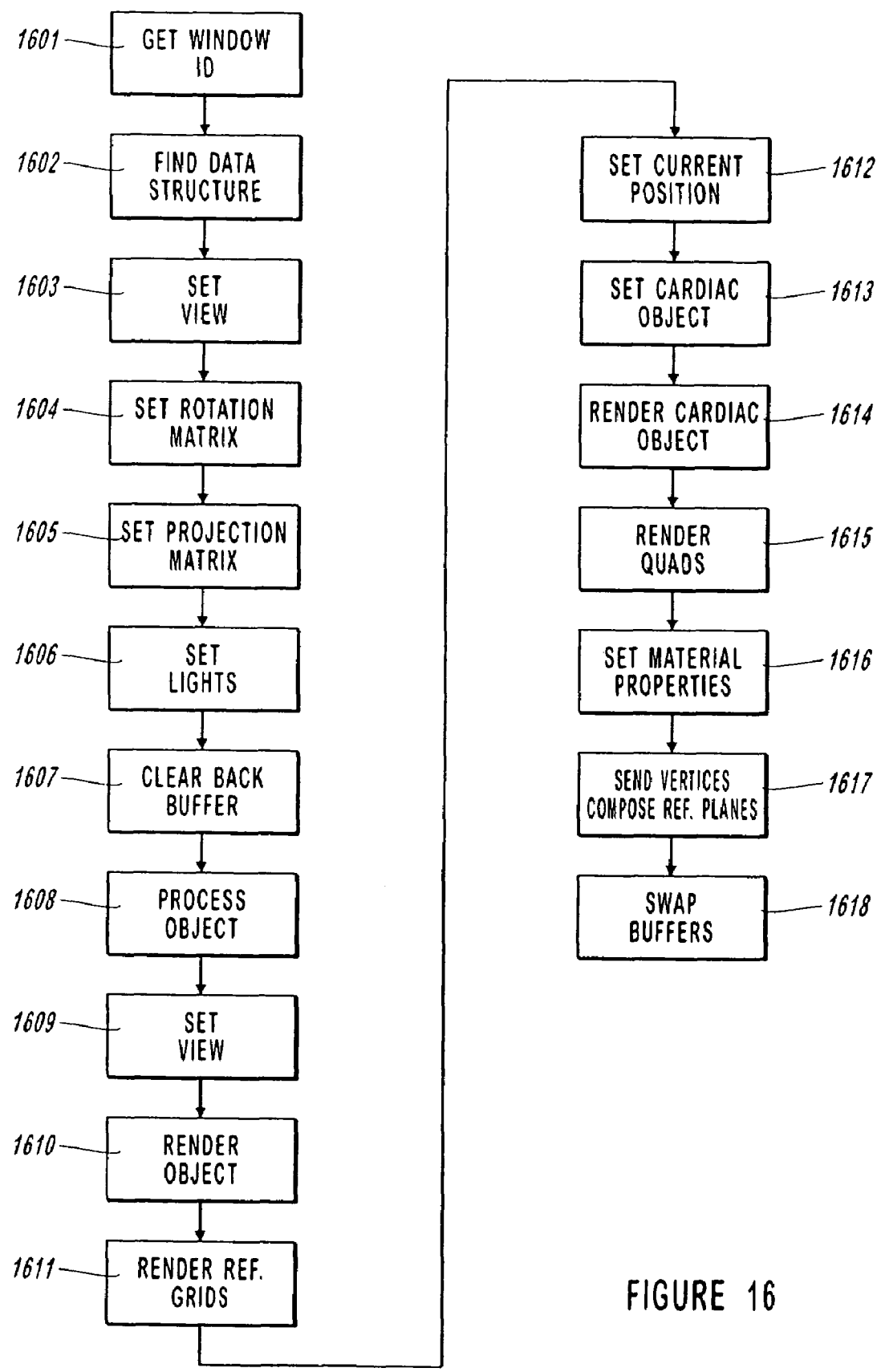
FIG. 16 is a software block diagram showing the logic steps of the image computation and rendering process of a preferred embodiment of the invention.

FIG. 16 is a software block diagram showing the logic steps of the image computation and rendering process of a preferred embodiment of the invention. This process begins with acquiring the window identification 1601 of the current rendering context. Next, the data structure is found 1602 corresponding to the current window identification. After which, the view is set 1603. A rotation matrix is set 1604. A projection matrix is set 1605. Lights are set 1606. The back buffer is cleared 1607. Object processing 1608 begins, and includes for each cardiac object, calling OpenGL to see material properties; shift left one inter-cardiac-object distance; push the modelview matrix, shift x,y, and z directions; call OpenGL utility toolkit to render the cardiac object; set the top cardiac object material properties, call OpenGL quadries function to render top cardiac object; set top cardiac object material properties, call OpenGL quadrics function to render bottom cardiac object and pop modelview matrix. Next, the view is set 1609, as above. The respiratory object is rendered 1610, by setting OpenGL to render quad strips, for each polygon strip set material properties, and send vertex to OpenGL. Reference grids are rendered 1611 by setting material property of the cardiac reference grid. The current position is set 1612 to be the ideal position of the newest cardiac object, that is the position corresponding to a patient in ideal health. The cardiac object material properties are set 1613. The OpenGL utility toolkit is called to render 1614 the cardiac object. Next, OpenGL is set to render quads 1615. After which the material properties of the reference planes are set 1616. Vertices that compose the reference planes through the OpenGL pipeline are sent 1617 and buffers are swapped 1618. Buffer swap is a window system defendant function.

Figure 17:
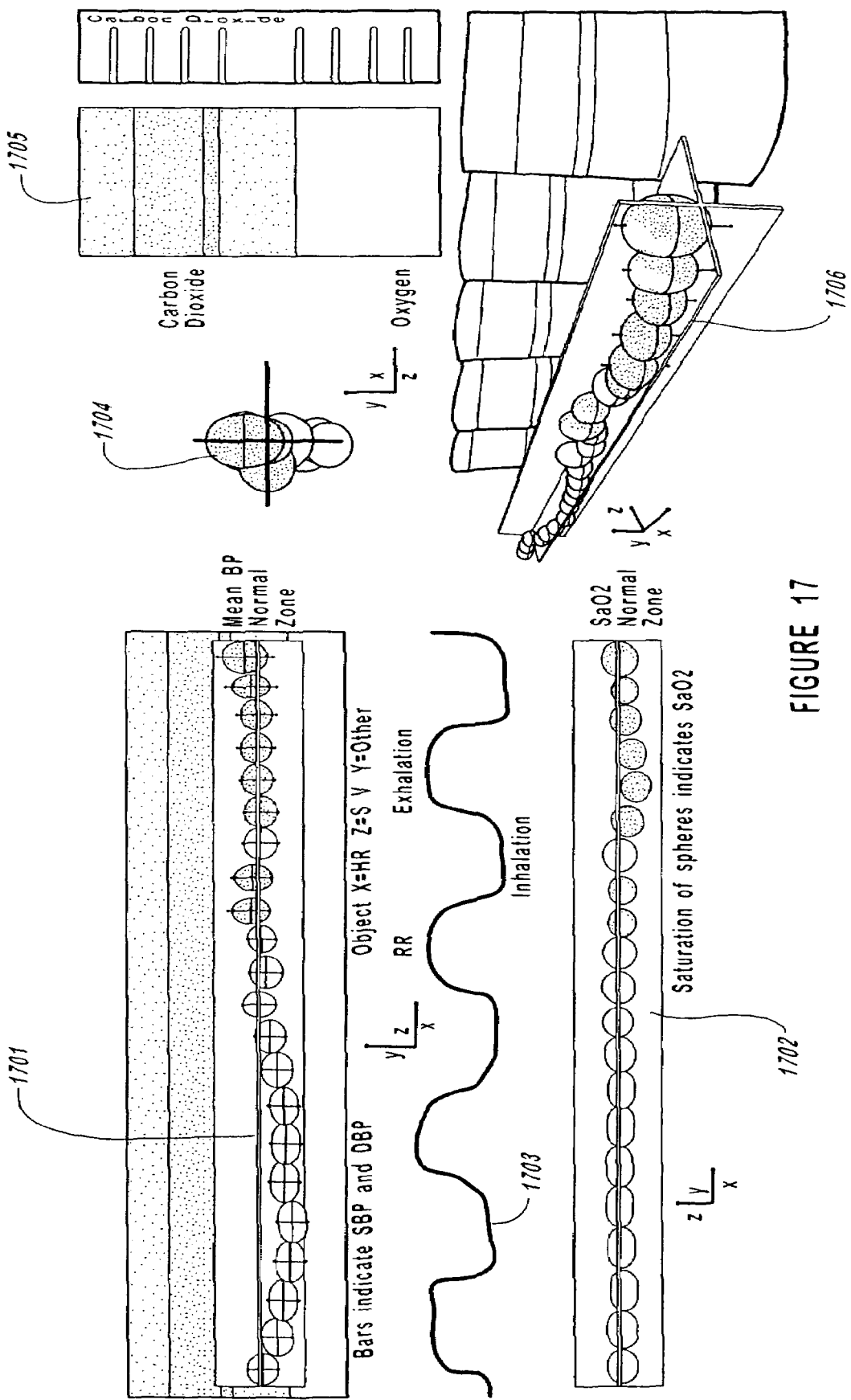
FIG. 17 is a photograph of the 3-dimensional display of a preferred embodiment of the invention.

FIG. 17 is a photograph of the 3-dimensional display of a preferred embodiment of the invention. The 3-D view shown at lower right 1706 provides a comprehensive, integrated and interactive view of all physiological data, and shows the interaction between the different objects in relation to the reference frame. This view can be manipulated by the user to fit specific application needs. The front 1701, side 1704, 1705 and top views 1702 show how the same data appears from different vantage points. In this figure these views 1701, 1702, 1704, 1705 show the interaction between the cardiac object, the reference frame and the respiratory object, with the side view 1704 providing a target for optimum efficiency of the cardiac system 1705 shows the level of gas concentration in the lungs and overall tidal volume in the respiratory system. This FIG. 17 is a representation of a true 3-D model of the physiologic data. The circle 1703 shown is the top view of the respiratory waveform showing CO2 content in the lungs and inspiration and expiration values. In 1703, a real time display, the object grows and shrinks with each heartbeat. Its height is proportional to the heart's volume output and its width is proportional to heart rate. The gridframe (or reference framework) shows the expected normal values for stroke volume and heart rate. The position of this object in the vertical direction of the display is proportional to the patient's mean blood pressure. This graphic objects shape and animation provides a useful graphical similarity to a working heart. In the preferred embodiment, the background is colored to show inspired and expired gases. The height of the "curtain" is proportional to tidal volume, while the width is proportional to respiratory rate. The colors, which are, displayed in the preferred display show the concentrations of respiratory gases. Time is set to move from right to left, with the present or current conditions shown at the "front" or right edge of each view. Past states remain to provide a historical view of the data.

Figure 18:
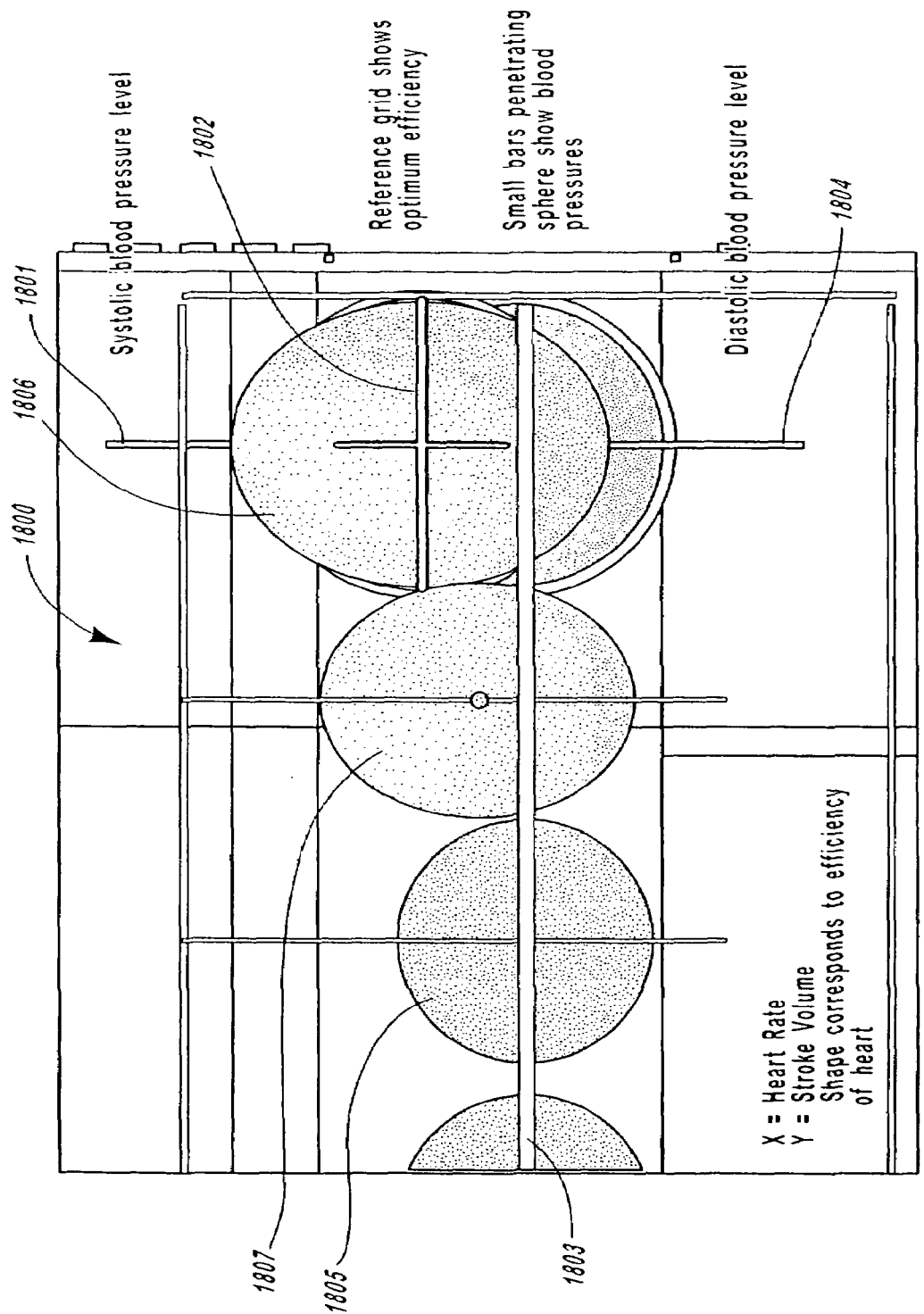
FIG. 18 is a close-up front view of the cardiac object and the associated reference grid of a preferred embodiment of the invention.

FIG. 18 is a close-up front view of the cardiac object and the associated reference framework of a preferred embodiment of the invention. The upper limit of normal blood pressure value is shown 1800 on the reference frame. The systolic blood pressure level is indicated by the bar 1801 penetrating the cardiac sphere 1806. The height 1802 of the sphere 1806 is proportional to cardiac output, which shows the optimum efficiency of the heart. The width of the sphere 1806 is proportional to 1/heart rate. The elevation of the sphere 1806 is an indication of mean blood pressure, where the center reference gridline is a normal mean blood pressure 1803. The lower limit, or diastolic blood pressure 1804 is shown by the length of the bar extending downward from the sphere 1806. Previous historical values for the sphere 1806 are also provided in 1805, 1807.

Figure 19:
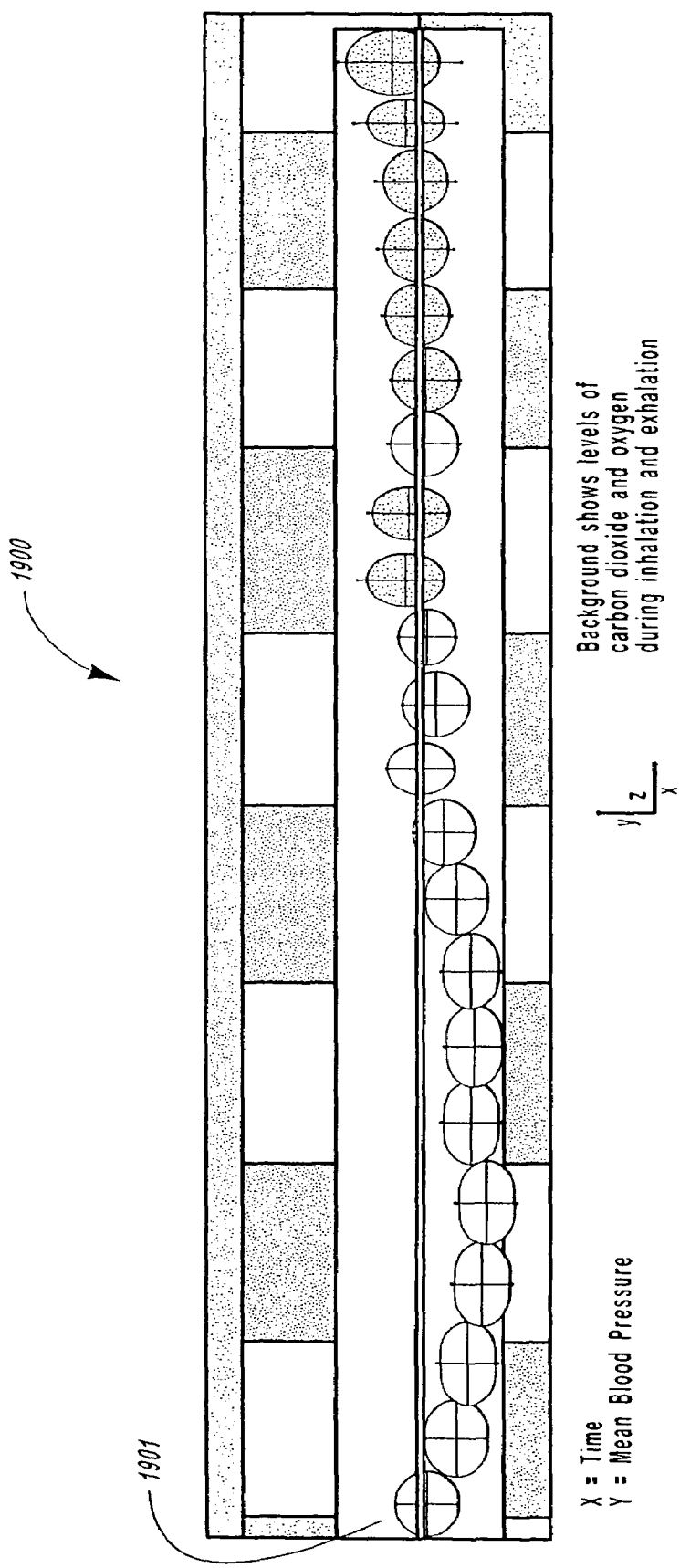
FIG. 19 is a view of the front view portion of the display of a preferred embodiment of the present invention showing the cardiac object in the foreground and the respiratory object in the background.

FIG. 19 is a view of the front view portion of the display of a preferred embodiment of the present invention showing the cardiac object in the foreground and the respiratory object in the background. This view 1900 provides a more quantitative image of the hemodynamic variables, stroke volume, blood pressure 1901 and heart rate. The "normal" reference lines are more apparent. In the preferred embodiment, respiration is shown by changes in the background color.

Figure 20:
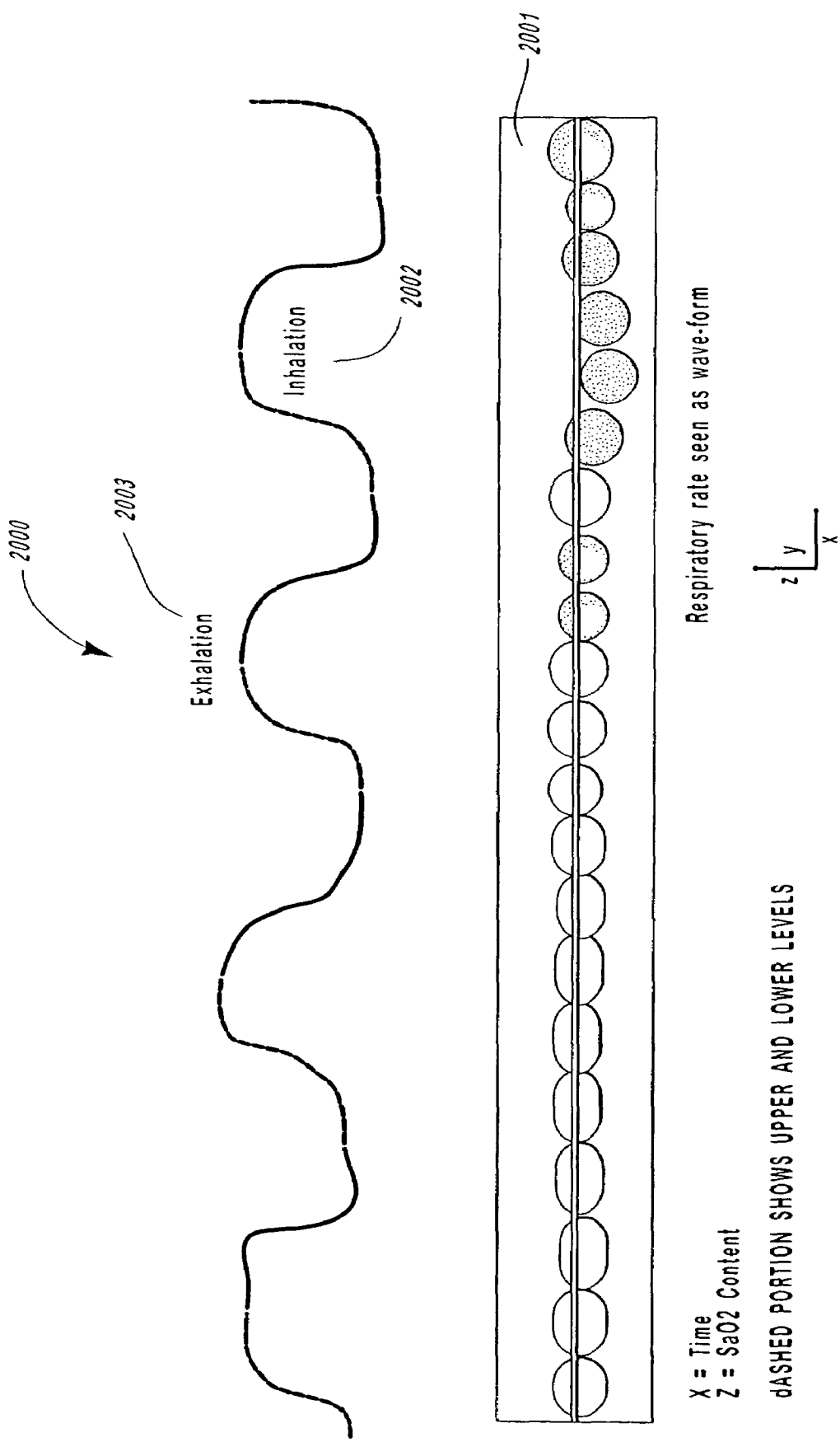
FIG. 20 is a view of the top view portion of the display of a preferred embodiment of the present invention showing the cardiac object toward the bottom of the view and the respiratory object toward the top of the view.

FIG. 20 is a view of the top view portion of the display 2000 of a preferred embodiment of the present invention showing the cardiac object toward the bottom of the view and the respiratory object toward the top of the view. Inhaled gas 2002 and exhaled gas 2003. C02 concentrations and oxygen saturation of the arterial blood 2001 versus time are also shown.

Figure 21:
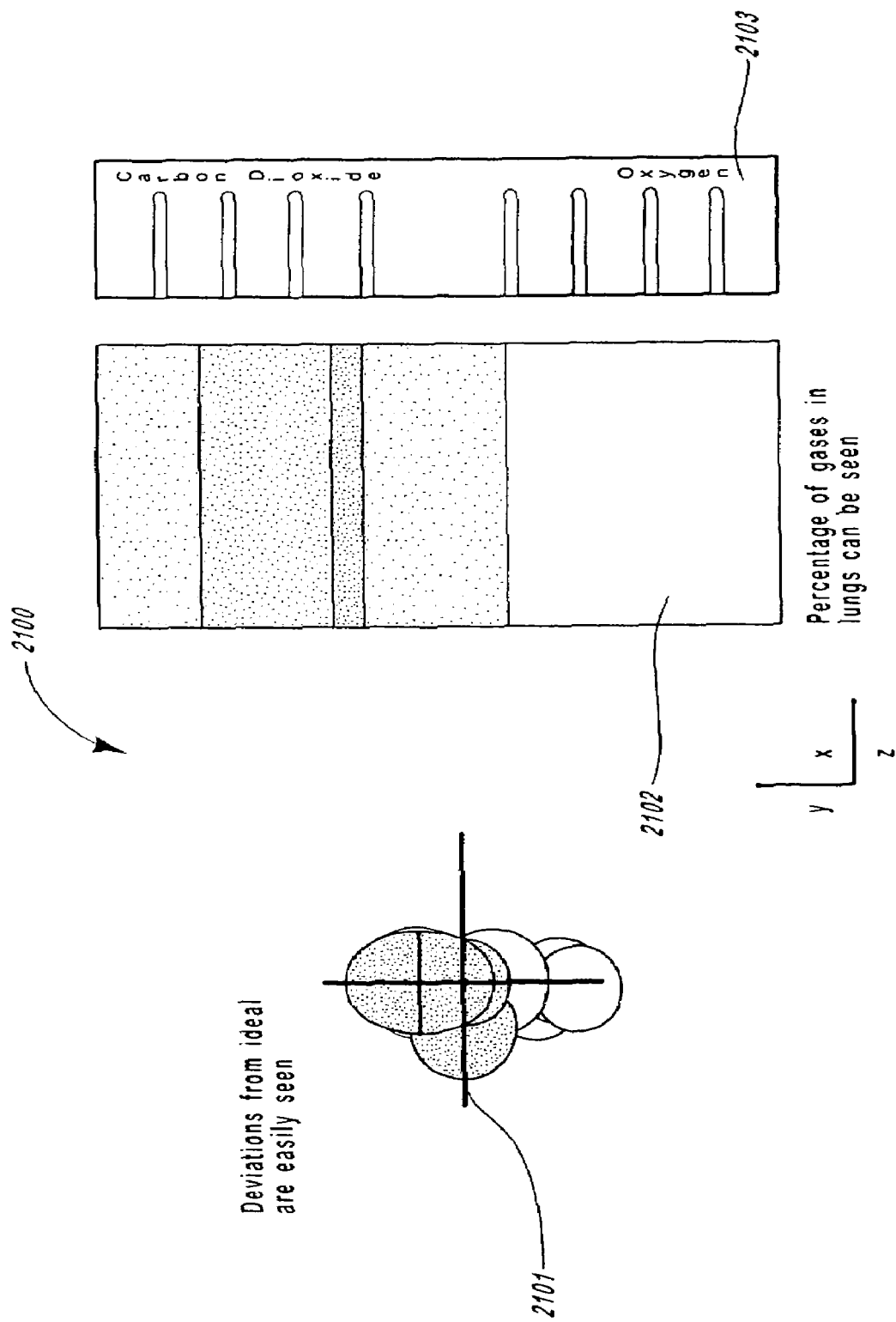
FIG. 21 is a view of the side view portion of the display of a preferred embodiment of the present invention showing the cardiac object to the left and the respiratory object to the right.

FIG. 21 is a view of the side view portion of the display of a preferred embodiment of the present invention showing the cardiac object to the left and the respiratory object to the right. Gas concentration in the lungs 2101, a calibrated scale for gas concentration 2103, blood pressure 2100, and oxygen saturation 2101 are shown. The end view, shown here in FIG. 21, is especially useful during treatment, where the goal is to bring the variables back to the center or normal state. Functional relationships can be added to this view to predict how treatment can be expected to bring the variables back to normal.

Figure 22:
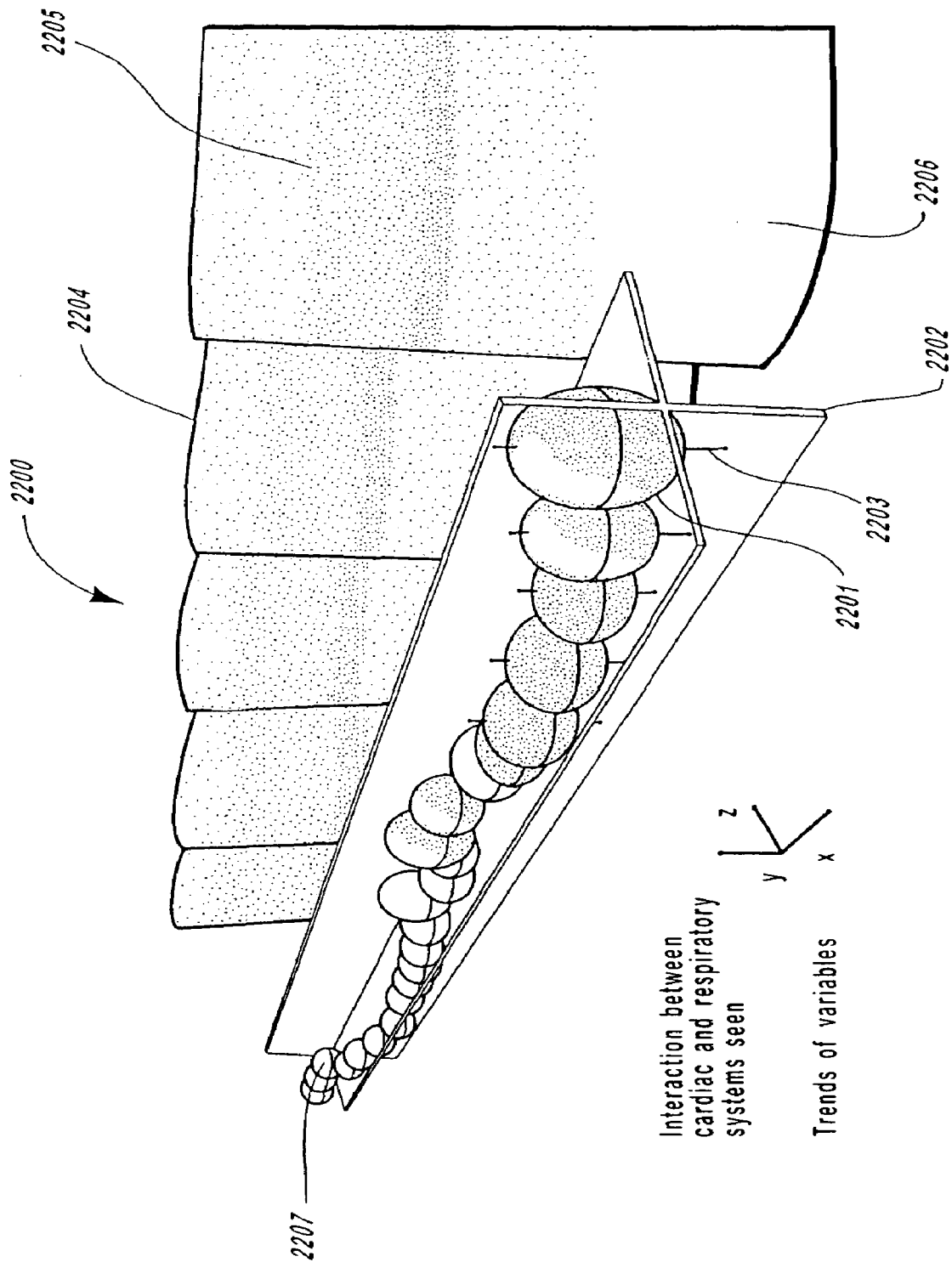
FIG. 22 is a view of the 3-D perspective view portion of the display of a preferred embodiment of the invention showing the cardiac object in the left foreground and the respiratory object in the right background.

FIG. 22 is a view of the 3-D perspective view portion of the display of a preferred embodiment of the present invention showing the cardiac object in the left foreground and the respiratory object in the right background. This view 2200 provides a comprehensive, integrated and interactive view of nine physiological variables. The sphere 2201 grows and shrinks with each heartbeat. Its height is proportional to the heart's stroke volume and its width is proportional to heart rate. This graphic object 2201 offers useful similarity to a beating heart. The gridframe 2202 shows the expected normal values for stroke volume and heart rate. The position of this object 2201 on the screen is proportional to the patient's mean blood pressure. The ends of the bar 2203 drawn vertically through the center of the heart object show systolic and diastolic blood pressure. In the preferred embodiment of the invention, the background 2204 is colored to show inspired and expired gases. The height of the "curtain" 2205 is proportional to tidal volume. The width of each fold 2206 is proportional to respiratory rate. In the preferred embodiment colors are used to show the concentrations of respiratory gases. Time moves from right to left with the present condition shown at the "front" or right edge of the view 2200. Past states 2207 remain to permit a historical view of the data.

A further embodiment of the invention will now be described in relation to FIGS. 23-28. In order to better understand this additional embodiment, it is valuable to understand that humans are largely visual creatures and the present embodiment of invention includes a graphical user interface for providing feedback regarding a patient's cardiovascular system. Particularly, this diagnostic interface is valuable to a doctor, an anesthesiologist, and similar medical personnel.

Recent cognitive research has indicated that the human mind is better able to analyze and use complex data when it is presented graphically, rather than in textual or numerical formats. For example, the application of perceptual grouping can facilitate the understanding of the relationships between individual pieces of data. Grouping by color, similarity, connectedness, motion, sound and other methods is valuable. The more complex and critical the information, the more imperative it is to communicate the information effectively.

Proper presentation of information also affects the speed and accuracy of higher-level cognitive operations. Therefore, it is valuable for information to be presented in a manner that facilitates the user's ability to process the information and minimize mental transformations that are applied to the data. Providing information in an integrated way can increase an anesthesiologist's or medical clinicians' situational awareness and reduce the risk of patient injury.

To monitor an anesthetized patient, the medical clinician watches over 30 interrelated variables. This task is very demanding, and requires the clinician to keep a high level of situational awareness while performing other duties, such as caring for the patient, filing out patient record, etc. Prior art displays show the information in a sub-optimal format such as waveforms and numeric values. In contrast, the display of the present invention organizes measured and modeled physiological information into relevant data sets or critical functions. These data sets can be mapped as graphical objects (e.g., cubes, spheres, cylinders, prisms) that work as metaphors of the critical functions of the cardiovascular system.

There are a number of cardiovascular variables that have important clinical information about the patient's cardiovascular state.

Central venous pressure (CVP, mmHg) measures the blood pressure after gas exchange in the systemic tissues and organs.

Mean pulmonary artery pressure (PAP, mmHg) is the blood pressure in the lungs. When PAP is high, such as in right heart failure, fluid tends to cross the pulmonary-capillary membranes and collect in the lung's alveoli.

The pulmonary vascular resistance (PVR, dynes/sec/cm$^2$) indicates vasoconstriction or vasodilatation of the pulmonary vasculature.

Mean left arterial pressure (LAP, mmHg) in the pulmonary vein is an indicator of left heart preload.

Cardiac Output (CO, ml/min) is the blood flow through the heart and is a function of heart rate (HR, beats/min), and stroke volume (SV, ml): CO=HR×SV Mean arterial pressure (MAP, mmHg) is a primary clinical monitoring variable.

The systemic vascular resistance (SVR, dynes/sec/cm$^5$) is an indicator of arterial vessel constriction or dilation.

Blood is the substrate for oxygen transport. SaO2 is the ratio of oxygen saturated hemoglobin in the arterial system.

The present invention provides a display with uniform, regularly spaced elements to create a smooth balanced design when the monitored variables are normal, and the display can also include a reference frame. This provides a clinical monitor which aids in detecting rapid change. When the patient status is abnormal and deviations from a smooth balanced design occur, then these changes are perceived very quickly because the normal shapes are pre-attentively processed. That is to say that the objects "pop out" from their surroundings.

Figure 23:
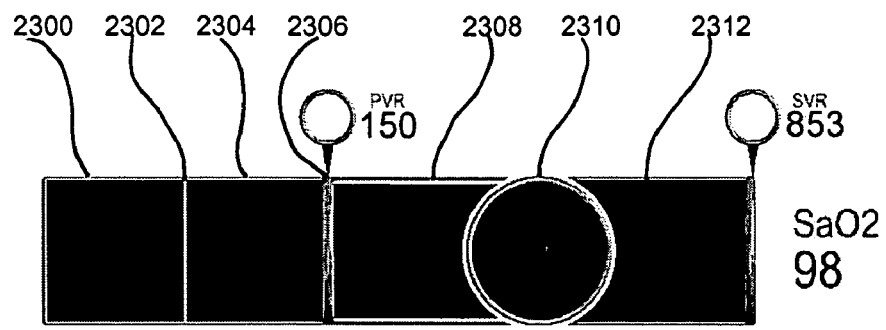
FIG. 23 illustrates a diagrammatic and anatomical display of blood flow through the cardiovascular system.

FIG. 23 illustrates that the objects in the display are spatially located to show a diagrammatic and anatomical organization of the flow of blood through the cardiovascular system. In addition, the functional relationships of cardiovascular physiology are illustrated by integrating related hemodynamic variables. From the left, venous blood returning from the systemic capillaries flows into the vena cava 2300. The right heart 2302 pumps the deoxygenated blood through the pulmonary arteries 2304 to the lungs 2306, which is the site of gas-exchange. Oxygenated blood in the pulmonary veins 2308 flows to the left heart 2310 where it is pumped via the aorta 2312 to the systemic tissues. This arrangement places all relevant measurements together in context to allow rapid understanding and diagnosis.

This organization highlights important concepts such as left heart preload, afterload and cardiac output. By arranging and placing relevant variables together, the graphical interface depicts more clearly the relationships between variables and generates display patterns consistent with a patient's changing cardiovascular physiology.

The display conveys the look of a pipe from a side view and can be a geometric graphic metaphor for a blood vessel. Movement of intensity or color indicators out of the borders of the pipe (e.g., vertical movement) can represent a change in blood pressure. In the cardiovascular system, blood pressure is often used as a surrogate for a patient's volume status. As the blood pressure increases for a portion of the cardiovascular system, the corresponding object becomes larger by increasing in the vertical direction. In other words, the color or graphic filling the object will expand outside the volumetric reference frames surrounding the object. Thus, the objects' movement provides a dual notion of the patient's pressure and volume status. In addition, abnormal changes in pressures can have clinical meaning. For example, abnormally high LAP or preload may mean that the left heart is not functioning optimally. The outline or border of the pipe can represent normal pressure for each cardiovascular object. The object's size in relation to the reference pipe conveys whether blood pressure is normal, high or low with respect to an average patient's physiology. Alternatively, the shapes used for suggesting the pipe can be oriented in a perspective view using cylinders. Orienting cylinders in a perspective view can help add to the suggestion of physiological ordering in the user interface.

In addition, the display was designed using simple shaped and uniformly spaced elements to create a smooth balanced design. Thus, when variables are normal, they fall within a uniform reference frame. The design of the present invention was intended to promote rapid detection of change just as artificial horizon and polygon displays improve performance in detecting events in aviation. When patient variables are abnormal, the deviations from normal are quickly noticed, because the normal shapes are pre-attentively processed. That is, the abnormally shaped objects clearly emerge from their surroundings.

Figure 24:
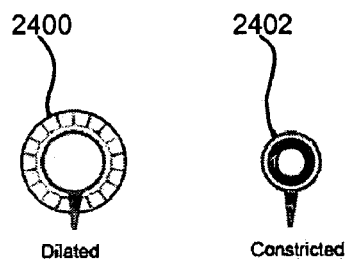
FIG. 24 illustrates circles that represent vascular tone.

Vascular tone in the pulmonary and systemic cardiovascular systems is shown as circles and represented as a cross-section of the pipe in FIG. 24. When resistance is high, the vessels are constricted and the circle is filled 2402. When resistance is low, the vessels are dilated and the circle is expanded 2400.

Figure 25:
FIG. 25 illustrates a graphic representation of when a heart is not receiving adequate oxygen.

The left heart is responsible for delivering blood to the vital organs and the tissues represented as a sphere or circle. Its visual dominance is purposely stated due to the severe consequences of heart failure. The diameter of the sphere is proportional to the stroke volume. When stroke volume is low (poor contractility), then the heart object becomes small, and a large heart object represents a large volume of blood ejected during each heartbeat. Again, a gray circle around the object reference frame indicates the physiology. Animated "beating" of the sphere indicates heart rate. Furthermore, if the heart is not receiving adequate oxygen (myocardial ischemia, computed by ST segment analysis of the electrocardiogram (ECG)), then it changes shape drastically in order to elicit prompt attention. This is illustrated in FIG. 25. Other changes in the patient's electrocardiogram that can indicate potential problems with the heart may be graphically displayed within or mapped to the heart object, such as premature ventricular contractions, atrial fibrillation, ventricular tachycardia, etc. An object for the right heart is intentionally missing because sensors that distinguish between left and right cardiac output continuously do not currently exist, but a right heart may be added if this variable is someday feasible to measure.

Figure 26:
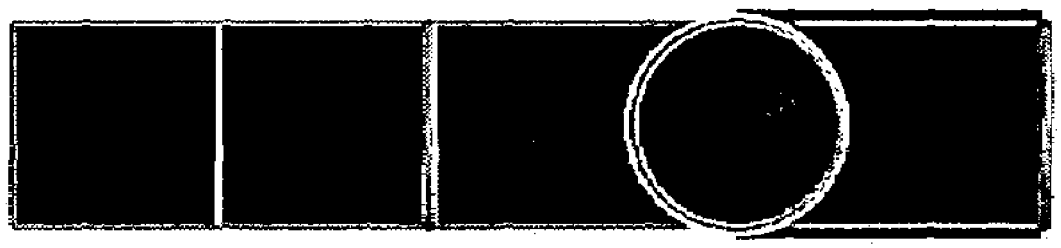
FIG. 26 illustrates an intensity change representing changes in blood saturation.

Finally, the color of the LAP, left heart, and MAP objects is proportional to the SaO2. Brain and vital organ damage rapidly ensues if the patient has even short durations of arterial blood desaturation. If the arterial blood is well oxygenated (SaO2>93%), then the objects' color will be lighter or bright red. As arterial blood begins to desaturate, when the patient has no ventilation for example, the color rapidly changes from lighter to darker or red to purple (87%>SaO2>93%) to blue (SaO2<87%). This intensity or color change is illustrated in FIG. 26.

In addition, the emergent shapes invoke a diagnosis by the clinician because the objects look similar to the way an anesthesiologist may envision the cardiovascular elements in the mind's eye. The design and orientation of a display effectively depicts the patient's cardiovascular status to the clinician in terms of:

(1) preload (filling pressures into the left ventricle of the heart, shown by the LAP object), (2) contractility (heart pumping effectiveness, heart muscle health, depicted by stroke volume, heart rate, and electrocardiogram (ECG) analysis such as ST-segment analysis, shown by the color, shape and size of the left heart object), (3) afterload (the force with which the left ventricle works to eject blood into the systemic circulation, depicted by MABP and SVR)

Figure 27:
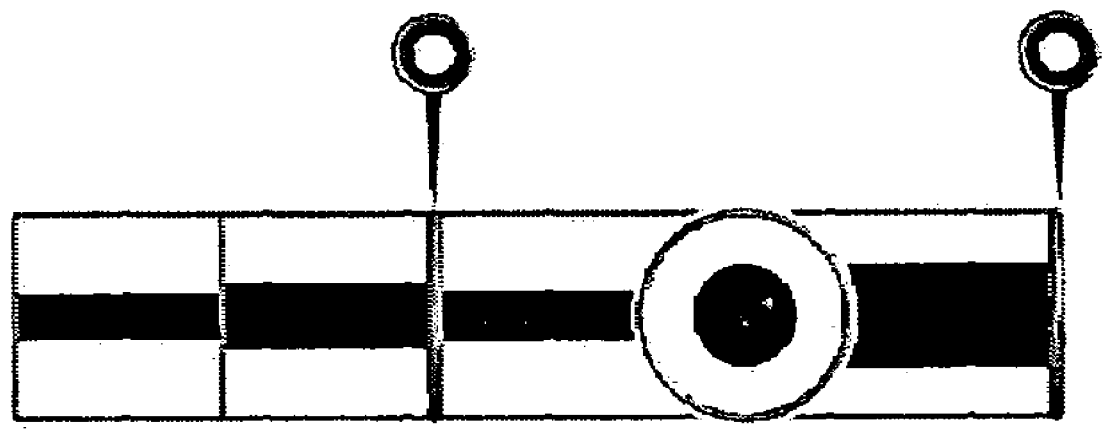
FIG. 27 illustrates a hypovolemic patient that looks like a partially empty pipe.
Figure 28:
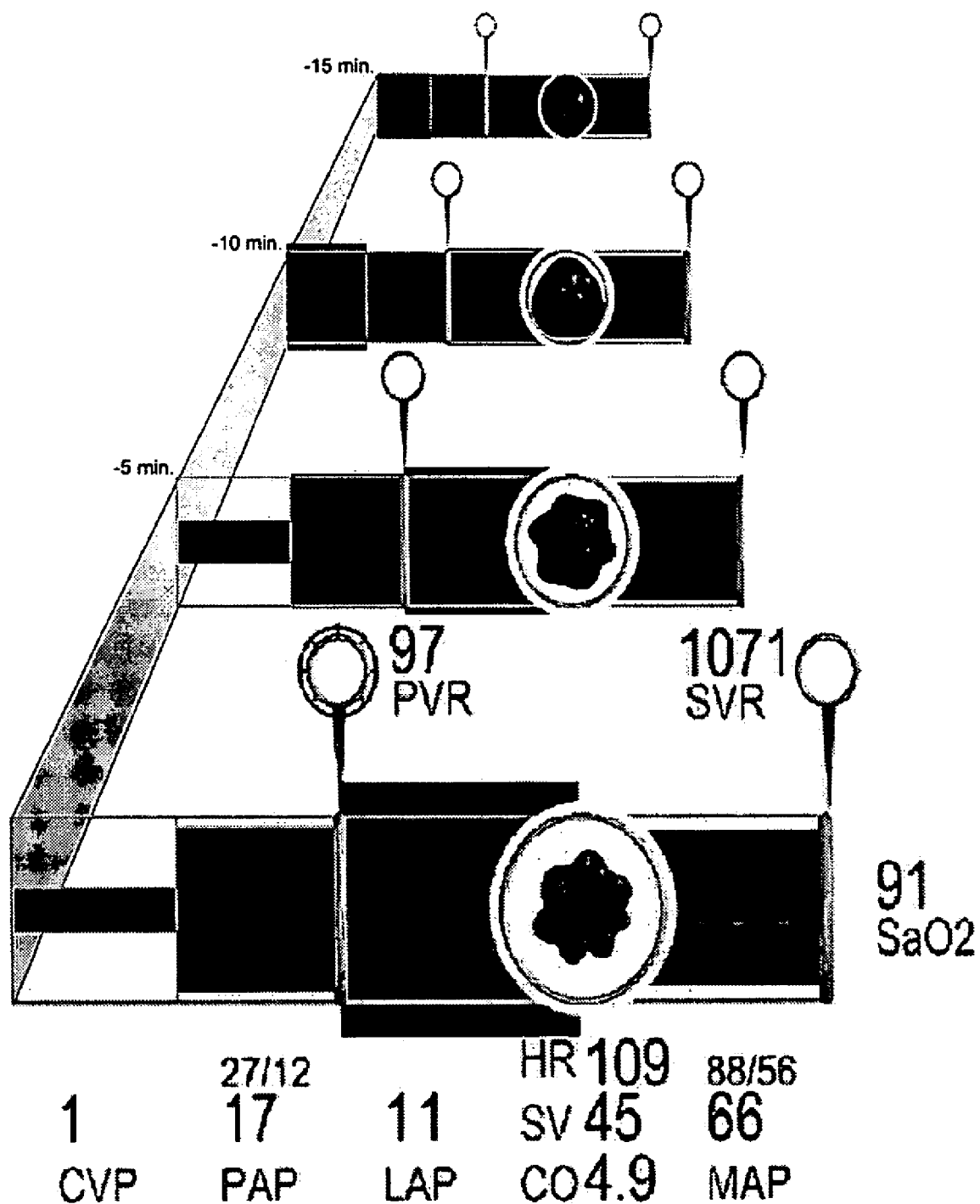
FIG. 28 illustrates the use of an embodiment of the diagnostic display for a cardiovascular system over time.

(4) volume status (uses pressures and resistances to determine whether the patient has lost significant amounts of blood, depicted by CVP, Stroke Volume, HR and MABP), (5) oxygen saturation of the blood (shown by the color of the objects) For example, during hypovolemia (blood loss), blood pressure falls, systemic vascular resistance increases, and cardiac output falls which shows up as smaller objects narrowed down like a nozzle with SVR increased to compensate for hypotension. The hypovolemic patient is referred to as a dry patient and the resultant graphic shows an image that looks dry or like an empty pipe as illustrated in FIG. 27. In FIG. 28, a representation is shown of the use of one embodiment of the present invention over a given time period. The elements of this invention are valuable because they support naturalistic decision-making by providing holistic cardiovascular patterns that are readily learned and applied to rapid diagnosis.

It is to be understood that the above-referenced arrangements are illustrative of the application for the principles of the present invention. It will be apparent to those of ordinary skill in the art that numerous modifications can be made without departing from the principles and concepts of the invention as set forth in the claims.

The invention claimed is:

1. A medical diagnostic display method for providing an integrated graphic representation of a patient's cardiovascular system for diagnostic purposes and display to a user, comprising:
displaying a plurality of blood flow graphic objects representing a sequential anatomic ordering of blood flow, the plurality of blood flow graphic objects being based on multiple diagnostic measurements made from the patient's cardiovascular system; and
displaying a heart graphic object representing a patient's heart status, the heart graphic object being displayed in sequential anatomical ordering with respect to the blood flow graphic objects.

2. A medical diagnostic display method as in claim 1, further comprising displaying the heart graphic object and the plurality of blood flow graphic objects having volumetric reference frames.

3. A medical diagnostic display method for providing an integrated graphic representation of a patient's cardiovascular system for diagnostic purposes and display to a user, comprising:
displaying a venous object configured to represent a sequential anatomical ordering of venous blood flow;
rendering a heart object representing a patient's heart status, the heart object being displayed in sequential anatomical ordering with respect to the venous object; and
displaying an arterial object in anatomical association with the heart object, the arterial object being configured to represent oxygen saturation of arterial blood hemoglobin.

4. A medical diagnostic display method as in claim 3, wherein the medical diagnostic display is configured to depict a patient's cardiovascular processes in an anatomical ordering.

5. A medical diagnostic display method as in claim 3, further comprising displaying a vascular tone object, associated with the medical diagnostic display, the vascular tone object being rendered to represent vascular tone in the pulmonary and systemic cardiovascular systems.

6. A medical diagnostic display method as in claim 5, wherein the vascular tone object represents resistance of blood flow in systemic arteries.

7. A medical diagnostic display method as in claim 5, wherein the vascular tone object represents resistance of blood flow in a pulmonary system.

8. A medical diagnostic display method as in claim 3, wherein the displaying of the venous object further comprises displaying a plurality of venous objects.

9. A medical diagnostic display method as in claim 8, wherein displaying the plurality of venous objects further includes displaying a first venous object representing venous blood returning from capillaries into a vena cava.

10. A medical diagnostic display method as in claim 8, wherein displaying the plurality of venous objects further includes displaying a second venous object representing a flow of blood from a right heart through pulmonary arteries.

11. A medical diagnostic display method as in claim 3, wherein the heart object is displayed as a spherical object.

12. A medical diagnostic display method as in claim 11, wherein the heart object is displayed and animated to indicate a heart rate.

13. A medical diagnostic display method as in claim 11, wherein the displayed heart object is decreased in scale to represent low stroke volume.

14. A medical diagnostic display method as in claim 11, wherein the displayed heart object is increased in scale to represent an increased stroke volume.

15. A medical diagnostic display method as in claim 11, wherein the displayed heart object changes shape to represent changes in the electrocardiogram (ECG) waveform.

16. A medical diagnostic display method as in claim 11, further comprising displaying an aorta object which represents pumping of oxygenated blood to systemic tissues.

17. A medical diagnostic display method as in claim 3, wherein the plurality of venous objects further comprises displaying a lung marker.

18. A method for displaying organizing a plurality of diagnostic data for a patient's cardiovascular system in a graphic display for a user, wherein the patient's cardiovascular system has a direction of blood flow with an upstream and a downstream:
displaying a venous graphic object contained within a first reference frame that represents a normal status of the venous graphic object in the patient's cardiovascular system;
displaying an cardiac graphic object oriented downstream from the venous graphic object and representing a patient's heart status, the cardiac graphic object being contained within a circular reference frame that represents a heart's normal status; and
displaying an arterial graphic object located downstream from the cardiac graphic object, configured to represent oxygenated blood flow in relation to the cardiac graphic object, the venous graphic object being surrounded by a second reference frame that represents a normal status of the arterial object.

19. A method as in claim 18, wherein the heart graphic object is rendered as a spherical object.

20. A medical diagnostic display method for providing an integrated representation of a patient's cardiovascular system for diagnostic purposes for viewing by a user, comprising:

displaying a vena cava object configured to represent a venous blood flow from systemic capillaries into a vena cava;

displaying a right heart marker adjacent to the vena cava object, the right heart object representing pumping of deoxygenated blood;

displaying a pulmonary arteries object depicting the flow of deoxygenated blood from the right heart;

displaying a lung marker adjacent the pulmonary arteries object, representing oxygenation of blood from the pulmonary arteries;

displaying a pulmonary vein object adjacent to the lung marker and representing flow of oxygenated blood;

displaying a heart object representing a patient's heart status, the heart object being displayed in anatomical ordering with respect to the pulmonary vein object; and displaying an aorta object configured to represent oxygenated blood flow from a patient's heart to systemic tissues.

21. A medical diagnostic display method for providing an integrated graphic representation of a patient's cardiovascular system for diagnostic purposes and display to a user, comprising:

displaying a preload graphic object configured to depict filling pressures into a left ventricle of the heart;

displaying a contractility graphic object representing a patient's heart status, the contractility object being displayed in sequential anatomical ordering with respect to the preload graphic object; and displaying an afterload graphic object in association with the contractility object, the afterload graphic object being configured to represent left ventricle force when ejecting blood.

22. A medical diagnostic display method as in claim 21, further comprising displaying volume statuses being incorporated into the graphic representation of the preload graphic object, the contractility graphic object, and the afterload graphic object for viewing by a user.

23. A medical diagnostic display method as in claim 21, further her comprising displaying oxygen saturation statuses being incorporated into the graphic representation of the preload graphic object, the contractility graphic object, and the afterload graphic object.

* * * * *